US008268308B2

(12) United States Patent
Bensussan et al.

(10) Patent No.: US 8,268,308 B2
(45) Date of Patent: *Sep. 18, 2012

(54) MEANS FOR THE DIAGNOSIS AND THERAPY OF CTCL

(75) Inventors: Armand Bensussan, Paris (FR); Martine Bagot, Paris (FR); Laurence Boumsell, Paris (FR); Allessandro Moretta, Genoa (IT)

(73) Assignee: Institut National de la Sante et de la Recherche Medicale, Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/008,406

(22) Filed: Jan. 18, 2011

(65) Prior Publication Data
US 2011/0151472 A1 Jun. 23, 2011

Related U.S. Application Data

(62) Division of application No. 12/050,441, filed on Mar. 18, 2008, now Pat. No. 7,919,085, which is a division of application No. 10/450,818, filed as application No. PCT/EP01/15417 on Dec. 18, 2001, now Pat. No. 7,399,595.

(30) Foreign Application Priority Data

Dec. 18, 2000 (EP) .................................... 00403580

(51) Int. Cl.
*A61K 39/395* (2006.01)
(52) U.S. Cl. .................................................. 424/130.1
(58) Field of Classification Search .................. None
See application file for complete search history.

(56) References Cited

U.S. PATENT DOCUMENTS 7,919,085 B2 * 4/2011 Bensussan et al. ........ 424/130.1

OTHER PUBLICATIONS

Musette, P. et al. "Polymorphic expression of CD158k/p140/KIR3DL2 in Sézary patients", *Blood*, Feb. 1, 2003, p. 1203, vol. 101, No. 3.
Carrington, M. et al. *The KIR Gene Cluster*, Available from the NCBI Bookshelf (http://www.ncbi.nlm.nih.gov/books/bv.fcgi?rid=mono_003.TOC&depth=2), May 28, 2003, pp. pdf-1-pdf-48.
Ge, H. "UPA, a universal protein array system for quantitative detection of protein-protein, protein-DNA, protein-RNA and protein-ligand interactions" *Nucleic Acids Res.*, 2000, vol. 28, No. 2, pp. i-vii.
Ruzicka, J. et al. "Bioligand Interaction Assay by Flow Injection Absorptiometry" *Analytical Chemistry*, Dec. 15, 1997, pp. 5024-5030, vol. 69, No. 24.
Walter, G. et al. "Protein arrays for gene expression and molecular interaction screening" *Curr. Opin. Microbiol.*, 2000, pp. 298-302, vol. 3.

Nikolova, M. et al. "SC5, a novel functional cell structure expressed by Sezary syndrome cells" *J. Immunol.*, 1995, vol. 55, No. 1862, Supp. 1 (abstract).
Pende, D. et al. "The Natural Killer Cell Receptor Specific for HLA-A Allotypes: A Novel Member of the p58/p70 Family of Inhibitory Receptors That is Characterized by Three Immunoglobulin-like Domains and is Expressed as a 140-kD Disulphide-linked Dimer" *J. Exp. Med.*, Aug. 1996, pp. 505-518, vol. 184.
Linnemann, T. et al. "Identification of Epitopes for CTCL-Specific Cytotoxic T Lymphocytes" *Advanced in Experimental Medicine and Biology, Gene Therapy of Cancer*, 1998, pp. 231-235, vol. 451.
Derwent Publications Ltd., XP002167250 & RU 2104526, Feb. 10, 1998 (abstract).
Nikolova, M. et al. "Identification of cell surface molecules characterizing human cutaneous cell lymphomas" *Leuk. Lymphoma*, Apr. 2002, pp. 741-746, vol. 43, No. 4, abstract.
Musette, P. et al. "To the editor: Polymorphic expression of CD158k/p140/KIR3DL2 in Sezary patients" *Blood*, p. 1203, Feb. 1, 2003, vol. 101, No. 3.
Carrington, M. et al. "The KIR Gene Cluster" pp. pdf-1-pdf-48, 2003.
Alberts, B. et al., Molecular Biology of the Cell, $3^{rd}$ edition, 1994, p. 465, Garland Publishing, Inc.
Lewin, B. "Regulation of transcription" in *Genes VI*, Chapter 29, 1997, pp. 847-848, Oxford University Press, Inc., New York.
Fu, L. et al. "Translational regulation of human p53 gene expression" *EMBO Journal*, 1996, pp. 4392-4401, vol. 15.
Mallampalli, R.K. et al. "Betamethasone modulation of sphingomyelin hydrolysis up-regulates CTP: cholinephosphate cytidylyltransferase activity in adult rat lung", 1996.
Knox, S et al. "Treatment of Cutaneous T-Cell Lymphoma with Chimeric Anti-CD4 Monoclonal Antibody," *Blood*, Feb. 1, 1996, pp. 893-899, vol. 87, No. 3.
Lundin, J. et al. "Phase II study of alemtuzumab (anti-CD52 monoclonal antibody, Campath-1H) in patients with advanced mycosis fungoides/Sézary syndrome," *Blood First Edition Paper*, 2003, pp. 1-27.
Olsen, E. et al. "Pivotal Phase III Trial of Two Dose Levels of Denileukin Diftitox for the Treatment of Cutaneous T-Cell Lymphoma," *J. Clin. Oncol.*, Jan. 15, 2001, pp. 376-388, vol. 19, No. 2.
Christiansen, J. et al. "Biological impediments to monoclonal antibody-based cancer immunotherapy" *Molecular Cancer Therapeutics*, 2004, pp. 1493-1501, vol. 3, No. 11.
Topp, E. M. et al. "Antibody transport in culture tumor cell layers" *Journal of Controlled Release*, 1998, pp. 15-23, vol. 53.
Jain, R. "Barriers to Drug Delivery in Solid Tumors" *Scientific American*, Jul. 1994, pp. 58-65.
Dillman, R. O. "Monoclonal Antibodies for Treating Cancer" *Annals of Internal Medicine*, 1989, pp. 592-603, vol. 111, No. 7.
Weiner, L. M. "An Overview of Monoclonal Antibody Therapy of Cancer" *Seminars in Oncology*, Aug. 1999, Suppl. 12, pp. 41-50, vol. 26, No. 4.
Gura, T. "Systems for Identifying New Drugs Are Often Faulty" *Science*, Nov. 7, 1997, pp. 1041-1042, vol. 278.

* cited by examiner

*Primary Examiner* — Sean Aeder
(74) *Attorney, Agent, or Firm* — Saliwanchik, Lloyd & Eisenschenk

(57) ABSTRACT

The invention relates to a novel molecule, termed SC5 by the inventors, to a novel allelic form of p140, and to the biological applications of SC5 and p140 molecules, notably in the diagnosis and therapy of CTCL.

12 Claims, 14 Drawing Sheets

FIG. 7A     FIG. 7B

Figure 1A:
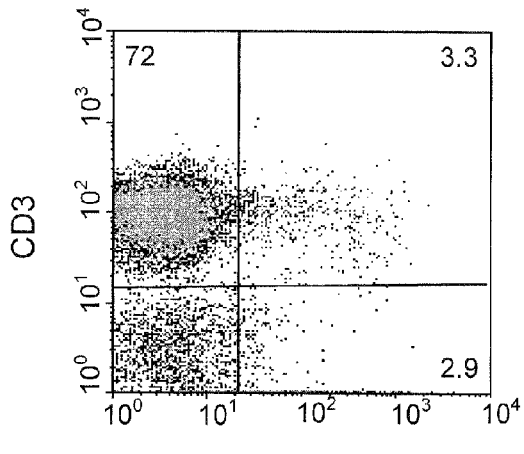

| Consensus | msltvvsmac vgffllqgaw pLMGGQDKPF LSARPSTVVP .GGHVALQCH YRRGFNNFML YKEDRSHVPI FHGRIFQESF |
|---|---|
| IMGPVTPAHA | |
| KIR3D cl 24 | 69 .......... .......... .......... Q......... .......... .......... .......... |
| | 69 |
| p140 cl 1.1 | .......... .......... .......... .......... R......... .......... .......... .......... |
| | 69 |

| Consensus | GTYRCRGSRP HSLTGWSAPS NP.VIMVTGN HRKPSLLAHP G.LLKSGETV ILQCWSDVMF EHFFLHREGI SEDPSRLVGQ |
|---|---|
| IHDGVSKANF | |
| KIR3D cl 24 | .......... .......... ...L...... .......... ..T....... .......... .......... .......... |
| | 159 |
| p140 cl 1.1 | .......... .......... ...V...... .......... ..P....... .......... .......... .......... |
| | 159 |

| Consensus | SIGPLMPVLA GTYRCYGSVP HSPYQLSAPS DPLDIVITGL YEKPSLSAQP GPTVQAGENV TLSCSSWSSY DIYHLSREGE |
|---|---|
| AHERRLRAVP | |
| KIR3D cl 24 | 249 .......... .......... .......... .......... .......... .......... .......... |
| | 249 |
| p140 cl 1.1 | .......... .......... .......... .......... .......... .......... .......... .......... |
| | 249 |

| Consensus | KVNRTFQADF PLGPATHGGT YRCFGSFRAL PCVWSNSSDP LLVSVTGNPS SSWPSPTEPS SKSGICRHLH VLIGTSVVIF |
|---|---|
| LFILLLFFLI | |
| KIR3D cl 24 | 339 .......... .......... .......... .......... .......... .......... .......... |
| | 339 |
| p140 cl 1.1 | .......... .......... .......... .......... .......... .......... .......... .......... |
| | 339 |

| Consensus | YRWCSNKKNA AVMDQEPAGD RTVNRQDSDE QDPQEVTYAQ LDHCVFIQRK ISRPSQRPKT P.TDTSVYTE LPNAEPRSKV |
|---|---|
| VSCPRAPQSG | |
| KIR3D cl 24 | 429 .......... .......... .......... .......... .......... .P........ .......... |
| | 429 |
| p140 cl 1.1 | .......... .......... .......... .......... .......... .......... .L........ .......... |
| | 429 |

| Consensus | LEGVF 434 |
|---|---|
| KIR3D cl 24 | ..... 434 |
| p140 cl 1.1 | ..... 434 |

FIG. 11

MEANS FOR THE DIAGNOSIS AND THERAPY OF CTCL

CROSS-REFERENCE TO RELATED APPLICATIONS

This application is a divisional of U.S. application Ser. No. 12/050,441, filed Mar. 18, 2008, which is a divisional of U.S. application Ser. No. 10/450,818, filed Jan. 9, 2004, now U.S. Pat. No. 7,399,595, which is the national stage of international application No. PCT/EP01/15417, filed Dec. 18, 2001, the disclosures of which are hereby incorporated by reference in their entireties, including all figures, tables and amino acid or nucleic acid sequences.

FIELD OF THE INVENTION

The present application relates to novel means for the diagnosis and therapy of T lymphomas, and more particularly of Cutaneous T Cell Lymphomas (abbreviated into CTCL). The invention indeed provides novel tumor markers which are universal for CTCL, and describes biotechnological and medical uses thereof.

BACKGROUND OF THE INVENTION

CTCL is a group of T lymphomas which primarily involve the skin. The CTCL group namely comprises transformed Mycosis Fungoides (abbreviated into transformed MF), Sézary Syndrome (abbreviated into SS), Lymphomatoide Papulosis (abbreviated into LP), and CD30+ lymphomas. Transformed MF is characterized by skin invasion of clonally-derived malignant T lymphocytes that phenotypically resemble mature T helper cells. LP and CD30+ lymphomas also develop in the skin. More aggressive forms of CTCL develop when the malignant cells become non-epidermotropic, and are associated with extra-cutaneous involvement. SS is a more aggressive form of CTCL that is characterized by a clonal expansion of CD4+/CD45RO+ T cells and the appearance of these malignant T cells in the blood. Most CTCL are CD4+ CTCL, but some rare CD8+ CTCL cases exist.

The biology of CTCL disease remains poorly understood, as it is difficult to identify the malignant cells, due to the lack of specific cell surface markers. In cutaneous lesions, it is therefore difficult to distinguish CTCL cells from reactive infiltrating (non-tumoral) T lymphocytes.

Diagnosis of T lymphomas such as CTCL is at present time mainly based on cytological and histological observations of the presence or absence of tumoral cells in a sample collected from a suspected body area (observation of histopathological aspect on skin biopsis and/or presence of SS cells in the blood, via detection of cells showing a cerebriform nucleus). Such a diagnosis method is not fully reliable, notably at the early stages of the transformation of skin lymphocytes into malignant lymphocytes. Such a diagnosis method does also not enable to stage the disease. Technically speaking, it is also time-consuming.

Today, therapy of CTCL is tentatively achieved by induction of tumoral cell apoptosis via non specific chemotherapy.

There is therefore still a need for more accurate and appropriate solutions to the problem of the diagnosis and therapy of diseases involving the proliferation of malignant T cells, such as CTCL.

SUMMARY OF THE INVENTION

In view of this prior art situation, the inventors now provide two molecules which give solutions to the problem of CTCL, diagnostic and therapy: one has been termed SC5 by the inventors, and the other one is the p140 molecule (p140 is also referred to as KIR3DL2).

The SC5 molecule of the invention appears as a biochemically and functionally new protein, of which apparent molecular weight is of 96 kD under reducing conditions. It has been isolated as the antigen of a monoclonal antibody that has been produced by the inventors. The hybridoma producing this monoclonal antibody has been deposited on Oct. 30, 2000 at the C.N.C.M. (C.N.C.M. Institut Pasteur; 25, rue du Docteur Roux, F-75724 Paris Cedex 15, France) in accordance with the Budapest Treaty (C.N.C.M. deposit number: I-2575). When expressed at the cell surface, and made to aggregate, SC5 molecules act as inhibitory receptors for cell activity and proliferation.

The second marker of the invention, i.e. p140, was already known to be an inhibitory receptor, but has been previously described only on sub-groups of NK cells and of CD3-CD8+ cells from healthy humans. The inventors now demonstrate that p140 is expressed at the surface of tumoral T cells such as CTCL cells. They further demonstrate that p140 is expressed at the surface of malignant CD4+ T cells, such as CD4+ CTCL cells, whereas those other receptors that are usually observed at the surface of NK cells (such as p58.1, p58.2, p70KIRs, CD94/NKG2A) are not found at the surface of malignant CD4+ T cells. Of further note is that p140 has not been observed by the inventors at the surface of CD4+ T cells collected from patients suffering from non-tumoral dermatological diseases such as inflammatory skin diseases (e.g. lupus, lichen), or toxic epidermal necrolysis. At the surface of tumoral CD4+ T cells, two allelic forms of p140 have been identified by the inventors: allelic form KIR3D clone 24 (SEQ ID No.1), and allelic form p140 clone 1.1 (SEQ ID No.3). Allelic form KIR3D clone 24 (SEQ ID No. 1) is a new polynucleotide encoding a new protein (SEQ ID No.2): KIR3D clone 24 (SEQ ID No. 1) displays five differences when compared to the previously described p140 clone 1.1 DNA sequence (SEQ ID No. 3), resulting in four amino acid substitutions in the mature protein (SEQ ID No. 2) when compared to p140 clone 1.1. mature protein (SEQ ID No. 4).

The inventors demonstrate that the SC5 and p140 both share the same technical following features:
  SC5 and p140 both are membranar differentiation antigens which are characteristic of malignant T cells, and notably of malignant CD4+ T cells,
  whichever form of CD4+ CTCL is concerned, there are malignant CD4+ T cells which express SC5 or p140 at their surface (usually both SC5 and p140 are expressed): SC5 as well as p140 indeed cover the whole range of CD4+ CTCL, and notably the Sézary Syndrome (abbreviated into "SS"), transformed Mycosis Fungoides (abbreviated into "transformed MF"), Lymphomatoide Papulosis (abbreviated onto "LP"), and CD30+ lymphomas,
  there exists such a link between the presence of SC5 or p140 at the surface of CD4+ T cells and the existence of a CD4+ CTCL, that a CD4+ CTCL diagnosis based on the analysis of the presence of SC5 or p140 at the surface of CD4+ cells collected from the suspected body area (e.g. sample of skin erythroderma when transformed MF is suspected, or sample of peripheral blood when a more aggressive CTCL form, such as SS, is suspected) has a reliability of more than 90%, preferably of more than of 95%, most preferably of 100% (among those patients who were tested up to now, the reliability is of 100%): indeed, according to the invention, it can be concluded that a CD4+ T cell is tumoral as soon as there are p140 molecules detected at the surface of these CD4+ T cells, or as soon as a percentage of SC5+ CD4+ T cells higher than the average standard level is measured (the average standard level is in the 1-15% range, generally in the 5-10% range), and there exists such a link between the presence of SC5 or p140 at the surface of CD4+ T cells and the existence of a CD4+ CTCL, that the percentage of CD4+ SC5+ T cells, as well as of CD4+ p140+ T cells, that is measured in a sample of peripheral blood collected from a patient for whom a Sézary Syndrome (SS) is suspected, substantially corresponds to the percentage of malignant SS cells that are actually present in the peripheral blood of this patient (within a ±10% range for SC5+ CD4+ cells, within a ±5% range for p140+ CD4+ cells): the SC5 and p140 markers of the invention therefore share the common particular technical feature of enabling to assess the staging of a SS.

To the best of the inventors' knowledge, SC5 and p140 are the first molecules which are described as having these common technical features.

The invention thus provides the first CTCL universal markers. No prior art product was known to be such a CTCL universal marker. The closest prior art product in this respect would be CD30 of which presence at the surface of malignant CD4+ T cells directs to the conclusion that the patient has a particular form of CD4+ CTCL which is referred to in the art as CD30+ lymphoma. CD30 is therefore a CTCL marker, but its reliability is limited to a particular form of CTCL (CD30+ lymphomas), and CD30 does not cover every form of CD4+ CTCL: for CD4+ CTCL such as SS, transformed MF, or LP, there does not necessarily exist a malignant CD4+ T cell which would express CD30 at its surface. CD30 uses in CTCL, diagnosis and therapy is thus restricted to a particular form of CTCL, whereas the markers of the invention advantageously cover the whole range of CD4+ CTCL.

In addition to the technical features shared with p140, SC5 has the further characteristic of being a positive indicator of proliferation and/or functional activity (e.g. cytokine profile) of non-tumoral T cells. The presence of SC5 at the surface of T cells is indeed positively linked with the activation status of non-tumoral T cells, such as normal (CD4+ and CD8+) T cells or virus-infected CD4+ T cells. SC5 is thus also a useful novel means for the diagnostic and therapy of T cell viral infections such as HIV-infection, and of inflammatory diseases such as those of the auto-immune type (e.g. rheumatoid arthritis such as spondyloarthropathis, or skin immune mediated diseases such as psoriasis, eczema, atopic dermatitis). SC5 is also a useful target for modulating graft-host reactions: the activation of SC5 transduces an inhibitory signal that can be used to inhibit the reactions that effector recipient cells may develop against a graft.

The invention also provides with products capable of binding to the SC5 new molecule, and in particular with monoclonal antibodies directed against SC5 (anti-SC5 mAbs). It is also provided with anti-SC5 monoclonal antibodies which are capable of modulating the proliferation and/or the functional activity of T cells, and notably of tumoral T cells such as malignant CTCL cells. In particular, the monoclonal antibody produced by hybridoma I-2575 is capable of inhibiting the proliferation and/or functional activity of T cells, and according to a particularly useful feature, is capable of inhibiting the proliferation and/or activity of malignant T cells such as malignant CTCL cells (see examples below). Compounds binding to SC5, but not aggregating them will prevent SC5 inhibitory signal transduction, or will prevent compounds to reach SC5+ cells (target masking).

More generally, compounds binding to SC5 or p140 may, according to the invention, be used as complement recruiting agents, as ADCC stimulators, or as vectors for therapeutic agents so as to prevent, palliate, treat T lymphomas, such as CTCL.

The invention therefore also relates to the diagnostic and therapeutic uses of SC5- or p140-binding compounds such as anti-SC5 and/or anti-p140 monoclonal antibodies, and of products directly-derived therefrom (e.g. humanized monoclonal antibodies, or monoclonal antibodies with a double CD4-p140/SC5 specificity).

DETAILED DESCRIPTION OF THE INVENTION

The invention thus provides a hybridoma deposited on Oct. 30, 2000 as deposit number I-2575 at the C.N.C.M. in accordance with the Budapest Treaty (C.N.C.M. Collection Nationale de Microorganismes, Institut Pasteur. 25 rue du Docteur Roux, F-75724-Paris Cedex 15, France), and a method for preparing an anti-SC5 monoclonal antibody which comprises cultivating hybridoma I-2575 under conditions suitable for the metabolism of the hybridoma cells (e.g. culture for three days at 37° C., with 5% $CO_2$ in a humid atmosphere at $2 \cdot 10^6$ cells per ml of appropriate culture medium such as RPMI 1640 medium Gibco BRL Cat. No. 21875-034, with 10% Fetal Calf Serum, penicillin 100 U/ml and streptomycin 100 microgram/ml).

The invention therefore encompasses the monoclonal antibody (mAb) which is produced by hybridoma I-2575, or which is obtainable from the culture supernatant of this deposited hybridoma. This mAb is a pentameric anti-SC5 IgM. It is a useful tool for the diagnosis and therapy of an inappropriate or undesired T cell proliferation and/or functional activity (cytokine profile), of an inappropriate or undesired IL-2 production. It inhibits the proliferation and/or functional activity of normal T cells, of virus-infected T cells (e.g. HIV-infected CD4+ T cells), and of malignant T cells, such as notably malignant CTCL cells.

The monoclonal antibody produced by hybridoma I-2575 enables the isolation of a protein, termed SC5 by the inventors. SC5 protein appears as a biochemically and functionally new molecule, with an apparent molecular weight of 96 kD under reducing conditions. It has been located in and on numerous PBL cells: normal T cells (both from CD4+ and CD8+ subsets), and in particular CD3+ T cells, CD45RO+ T cells, but also normal NK cells, B cells, granulocytes and macrophages. In addition, SC5 has been located in the cytoplasm of cells from other lineages and other species such as NIH/3T3 (ATCC CRL-1658) and CHO-K1 (ATCC CRL-9618).

In resting normal PBL cells, SC5 is mainly intracellularly located, but CD3 stimulation induces the transfer of SC5 to the cell membrane. Remarkably, SC5 has also been observed by the inventors on malignant T cells, such as malignant CTCL cells, and in particular malignant CD4+ CTCL cells, where they are mainly located at the cell surface (without any ex vivo CD3 stimulation).

As a further remarkable feature, SC5 surface expression has been observed for all the CTCL patients who were tested until now (see the examples below).

Another further remarkable feature of the invention is that the percentage of CD4+ T cells which co-express SC5 is statistically higher in patients developing tumoral CD4+ T cells than in healthy patients. The percentage of SC5+ CD4+ cells in CD4+ CTCL patients is significantly higher than the percentage observed in healthy patients (average standard percentage of SC5+ CD4+ cells is in the 1-15% range, generally in the 5-10% range). In the particular CD4+ CTCL case of Sézary Syndrome (SS), the percentage of CD4+ cells which co-express SC5 is furthermore statistically closely correlated to the percentage of malignant CTCL cells in the PBL of the CTCL patient: the percentage of SC5+ CD4+ T cells is substantially equal to the percentage of malignant CTCL cells (within ±10% of this percentage). SC5 protein is therefore a new molecule whose transmembrane expression at the cell surface is linked to an activation and/or proliferation status for non-tumoral T cells (such as virus-infected cells, e.g. HIV-infected cells, and such as normal CD4+ or CD8+ T cells), and to a malignant status for non-activated T cells. According to a remarkable feature, it enables a CD4+ CTCL-positive diagnosis with a confidence of more than 90% (actually of 100% of those humans who have been tested up-to-date).

A further outstanding feature of the invention is that the SC5 new molecule is capable of acting as an inhibitory receptor for cell proliferation and/or functional activity when expressed at the cell surface: SC5 aggregation induces a decrease in the proliferation and activity of the cell expressing it. For example, the anti-SC5 monoclonal antibody produced by hybridoma I-2575 (which is a pentameric Ig) inhibits the anti-CD3 induced proliferation of SC5+ cells such as normal CD3+ T cells collected from a human or an animal, or normal CD3+ T cell clones, and also inhibits the anti-CD3 induced in vitro proliferation of CTCL cells collected from a CTCL patient, and the in vivo natural proliferation of human CTCL cells in an animal model. This mAb also binds HIV-infected CD4+ T cells, and is therefore useful as an active principle in an anti-HIV drug intended for killing infected cells, and therefore reducing HIV propagation.

Several procedures enabling the isolation of the SC5 protein are available to the skilled person to whom a monoclonal antibody of the invention has been made available.

Standard procedures comprise recovering the SC5 molecules from a cell lysate by affinity chromatography, or by electrophoresis under reducing conditions.

All human or animal cells which the monoclonal antibody produced by hybridoma I-2575 recognizes as an antigen, or of which lysate gives an immuno-precipitation reaction with this monoclonal antibody, are appropriate cell sources for isolating the SC5 molecule. Such cells notably include normal cells (collected from a human or an animal, or cell clones) such as T cells, CD3+ T cells, CD45RO+ T cells, B cells, NK cells, macrophages, granulocytes. Appropriate cells also include tumoral cells such as malignant T cells, e.g. CD4+ CTCL cells collected from a CTCL patient, or tumoral clones such as the CTCL clone HUT78 (ATCC TIB-161).

Due to the wide range of appropriate cell sources, it will be understood that rough total blood cell or PBL may be directly used as a SC5 source without any further purification.

Normal cells enable the isolation of both the intracellular form and the transmembrane receptor form of SC5. When it is desired to isolate the SC5 receptor form, or a portion thereof, it may thus be preferable to use a source of SC5+ cells (i.e. cells expressing SC5 at their surface). Such a source includes normal cells as above-mentioned but that have been CD3-stimulated so that SC5 expression increases at the cell surface (see examples below for CD3 stimulation procedures). When total blood cells or PM, are used as a source of SC5+ cells, CD3 activation can be induced by incubation with a polyclonal activator such as PHA (obtainable from Wellcome) at a concentration of about 1 microgram per ml, because total blood cells or PBL also contain T cells and mononuclear cells. When a more homogeneous normal cell population is used as a source of SC5+ cells (e.g. only SC5+ NK cells), then CD3 activation is preferably performed by incubation with immobilized anti-CD3 antibodies, or alternatively wan both soluble anti-CD3 antibodies and polyclonal activator such as PHA. Optionally, a culture step may be performed before and/or after CD3 activation so as to increase cell amount (e.g. culture for 3 days in RPMI 10% fetal calf serum at 37° C., 95% humidity, and 5% $CO_2$). When it is desired to isolate SC5 in its intracellular form, then CD3 stimulation may be omitted.

Tumoral cells such as CTCL cells, and notably malignant transformed MF or SS cells, enable the isolation of SC5 molecules in their receptor form, without any required ex vivo CD3 activation: CTCL cells already express SC5 in a transmembranar location.

The invention therefore encompasses any isolated protein obtainable by:

(i) collecting cells selected from the group consisting of T cells, CD3+ T cells, CD45RO+ T cells, B cells, NK cells, macrophages, granulocytes, and stimulating the collected cells with immobilized anti-CD3 antibodies, or with both soluble anti-CD3 antibodies and PHA at 1 microgram/ml, or collecting malignant CTCL cells such as malignant CD4+ CTCL cells, or collecting cells selected from the group consisting of total blood cells and peripheral blood lymphocytes (PBL), and stimulating the collected cells with PHA at about 1 microgram per ml, (ii) lysing the cells under conditions enabling the dissociation of multimeric polypeptidic complexes, for example by incubation in a drastic lysis buffer containing Triton X-100 at 1%, (iii) recovering from the lysate the protein compound onto which the monoclonal antibody produced by hybridoma I-2575 binds under conditions enabling this monoclonal antibody to perform reactions of the antigen-antibody type (i.e. the compound which is recognized as an antigen by this mAb).

The amino acid sequence of the recovered protein compound can be obtained by any standard technique, such as mass spectrophotometry.

As above-indicated, the cells mentioned in step i. are activated cells, and therefore enables the isolation of SC5 in the form it has when it is a transmembrane receptor. If the SC5 source used in step i. consists of resting normal T cells (without ex vivo stimulation), the protein compound thus isolated will be SC5 in its cytoplasmic form.

When the cells selected in step i. are activated or malignant cells, lysis in step ii. therefore may be performed either on whole cells, or on the membranar fraction of these cells.

The lysis step itself can be achieved by any technique enabling the dissociation of multimeric polypeptidic complexes from each others. For example, cells (or their membrane fraction) may be incubated in a lysis buffer containing a drastic detergent such as Triton X-100 at about 1% for 1 hour at 4° C.; this enables the dissociation of the SC5 protein from the other cell components. If a mild detergent such as digitonin 1% or Bridg58 1% is used, then SC5 won't dissociate from those compounds which are naturally associated with it; the use of a mild detergent in the above step ii. therefore enables the isolation of SC5, and the further isolation of the SC5 transducers and effectors.

The invention therefore also encompasses any isolated compound obtainable by such processes.

The lysate obtained from step ii. is then incubated with the monoclonal antibody produced by hybridoma I-2575 under conditions appropriate for this mAb to perform reactions of the antigen-antibody type, such as coating the antibodies into microwells containing the cell lysate (e.g. 2 micrograms of the monoclonal antibody produced by hybridoma I-2575 for a lysate of $10^7$ cells) and incubating the monoclonal antibodies with the cell lysate for two hours at 4° C.

The step of recovering the compound onto which the monoclonal antibody produced by hybridoma I-2575 binds (step iii.) can be achieved by any technique available to the skilled person. Recovering under non reducing conditions enables the isolation of SC5 in its native conformation, and will be preferred when it is desired to retain the native biological properties of SC5.

Appropriate techniques for recovering SC5 protein under non reducing conditions namely include chromatography by affinity, and, for example:
  percolation of the lysate through a column in which the monoclonal antibody (mAb) produced by hybridoma I-2575 has been immobilized (e.g. by coupling this mAb onto agar beads and placing these beads inside said column); preferably, the lysate is mixed with a buffer which has a physiological pH, e.g. at a pH comprised between 6 and 8, such as 7, before percolation so as to make the percolation easier without substantially altering the conformation of the compounds contained in the lysate,
  rinsing the column with a buffer at the same physiological pH, and
  recovering the compound which has bound to the immobilized mAb, e.g. by elution with a buffer which disrupts the binding of the compound onto the mAb without substantially modifying the native conformation of the compound.

Such an elution buffer usually has a slightly acidic pH (usually comprised between 2 and 5, e.g. a pH of 3). For the preparation of a matrix which has an optimal orientation of antibody molecules, and which thereby enables antigen binding at a high efficiency, and for a one-step purification procedure for the isolation of membrane proteins, see e.g. Schneider et al. 1982 (J. Biol. Chem. 257: 10766-10769) of which content is herein incorporated by reference. The protein compound thus recovered is the isolated SC5 protein in its native form.

Alternatively, step iii. under non reducing conditions can be achieved by placing the lysate obtained from step ii. for immuno-precipitation with the monoclonal produced by hybridoma I-2575, and the immuno-precipitate thus obtained can be percolated through a column comprising antibodies capable of binding mice IgM. The protein compound which has bound onto the monoclonal antibody produced by hybridoma I-2575 is then recovered by elution similarly to what has been above described. The protein compound thus recovered is also the isolated SC5 protein in its native form.

Another standard way for recovering the SC5 protein (step iii.) is to proceed through electrophoresis under reducing conditions. This notably includes incubating the monoclonal antibody produced by hybridoma I-2575 with the lysate obtained from step ii. under conditions enabling this mAb to perform reactions of the antigen-antibody type, collecting the immuno-precipitate thus formed, separating the compounds contained in this immuno-precipitate under reducing conditions, and recovering the protein compound which has an apparent molecular weight of 96 kD. An alternative way to localize on the electrophoresis gel or membrane the desired SC5 protein (and to subsequently isolate it from the gel or membrane) is to proceed with a labeling step prior to lysis so that surface polypeptidic components of the cells are labeled (e.g. 125iode or fluorescent labeling with e.g. sulfo-NHS-LC-biotin), and to recover from the immuno-precipitate those compounds which bear the label. It has to be noted that if the labeling step is performed after lysis, then both the intracellular form and the trans-membranar receptor form of SC5 will be isolated (in this case, as above-indicated, non-activated T cells may be used as a SC5 source). Because denaturing conditions are used, the protein compound thus recovered is in a non native form: it still has the native amino acid sequence, but its native biological properties have been substantially lost. It is however the SC5 protein in its non-native conformation that is observed (and has to be searched for) when the biological sample to be tested has been treated under denaturing conditions (such as e.g. paraffin sections of skin sample). The SC5 protein in its non-native form may therefore be used for the production of monoclonal antibodies directed against it, such monoclonal antibodies being then useful for SC5 detection on denatured samples. If the SC5 protein in its native conformation is desired, portions of at least 10 amino acids of the denatured protein may then be sequenced (e.g. by mass spectrophotometry), oligonucleotides deduced from the sequenced portions may be synthesized, and then used as probes to screen a cDNA library obtained from SC5+ cells. The cDNA thus selected may the be produced and cloned into a cell under conditions enabling the production, and preferably the excretion, of the cDNA-encoded product by culture of the clone (e.g. via insertion of the SC5-encoding cDNA in a baculo virus vector and transformation of insect cells—e.g. Sf9 cells-, or via the vaccina virus and EBV cells, see Rindis Bacher 1995, J. Biol. Chem. 270(23): 14220-14228).

The invention therefore encompasses any isolated protein of which sequence is obtainable by:
  collecting cells selected from the group consisting of total blood cells and peripheral blood lymphocytes (PBL),
  stimulating the collected cells with PHA at 1 microgram/ml,
  labeling the stimulated cells with a polypeptide-specific label such as biotin,
  lysing the labeled cells by incubation in a lysis buffer containing Triton X-100 at 1%,
  submitting the lysate to immuno-precipitation with the monoclonal antibody produced by hybridoma I-2575,
  recovering from the immuno-precipitate the protein compound which bears the label,
  synthesizing the cDNA which encodes the protein sequence thus obtained,
  operably transfecting insect cells with this cDNA,
  recovering the protein produced by the transfected cells, e.g. with the monoclonal antibody produced by hybridoma I-2575,
or obtainable by:
  collecting cells selected from the group consisting of total blood cells and peripheral blood lymphocytes (PBL),
  stimulating the collected cells with PHA at 1 microgram/ml.
  lysing the labeled cells by incubation in a lysis buffer containing Triton X-100 at 1%,
  submitting the lysate to immuno-precipitation with the monoclonal antibody produced by hybridoma I-2575,
  recovering from the immuno-precipitate the protein compound which has an apparent molecular weight of 96 kD under reducing conditions,
  synthesizing the cDNA which encodes the protein sequence thus obtained,
  operably transfecting insect cells with this cDNA,
  recovering the protein compound produced by the transfected insect cells, e.g. with the monoclonal antibody produced by hybridoma I-2575.

The invention thus encompasses any isolated protein compound obtainable by any of the above-mentioned processes, as well as any amino acid sequence of such an isolated protein compound, and any isolated protein of which sequence comprises such a sequence.

Falls within the scope of the invention any solid support onto which a protein compound or protein of the invention has been placed. Such solid supports notably include sepharose beads.

The invention also encompasses any isolated DNA (or cDNA) of which sequence codes for an isolated protein of the invention. It also relates to engineered cells transfected by such a DNA, to engineered cells which excrete an isolated protein of the invention, and to isolated protein obtainable by isolation from the culture medium of such engineered cells.

The invention notably encompasses any cDNA obtainable by:
- collecting a cell population which consists of, or comprises cells onto which the monoclonal antibody produced by hybridoma I-2575 binds (i.e. onto which this mAb recognizes an antigen), or cells of which lysate would give an immuno-precipitation reaction with this monoclonal antibody, e.g. collecting cells selected from the group consisting of total blood cells and PBL,
- if the sole transmembranar form of SC5 is desired:
  - stimulating the CD3 pathway if said cell population mainly comprises or consists of non-activated cells (e.g. resting non-tumoral cells) so as to increase SC5 expression at the cell surface, e.g. by incubating the collected cell population with a CD3 activator (for example a polyclonal activator such as PHA at 1 microgram per ml when the collected cell population is PBL or total blood, or immobilized anti-CD3 antibodies, or both a polyclonal activator such as PHA and soluble anti-CD3 antibodies when the collected cell population is more homogeneous such as a cell population mainly comprising, or consisting of CD3+ T cells, or of CD45RO+ cells, or of NK cells, or of macrophages, or of granulocytes);
  - if the collected cell population consists of or mainly comprises activated cells (such as CD3-activated non-tumoral cells, or such as tumoral cells such as CD4+ CTCL cells), then CD3 stimulation is not necessary because SC5 location is already mainly transmembranar in these activated cells;
  - if it is desired to isolate both the intracellular form and the trans-membranar form of SC5, then non-activated cells are preferred and CD3 activation is omitted,
- extracting and purifying the whole mRNA population from said cell population (commercial kits are available for mRNA extraction and purification, e.g. a polydT column),
- synthesizing every complementary cDNA (with a reverse transcriptase, e.g. such as described in Seed B. and Arrufo A. 1987, Proc. Natl. Acad. Sci. USA 84: 3365-3369, of which content is herewith incorporated by reference),
- operably cloning each cDNA so that expression of this cDNA in this clone is possible under appropriate clone culture conditions, and cultivating every clone accordingly,
- selecting those clones which express a compound onto which the monoclonal antibody produced by hybridoma I-2575 binds when placed under conditions suitable for this monoclonal antibody to perform reactions of the antigen-antibody type, and/or those clones of which lysate would give an immuno-precipitation reaction with the monoclonal antibody produced by hybridoma I-2575 will be selected.
- optionally amplifying those clones that have been thus selected,
- recovering the inserted cDNA from the selected clones.

The cDNA thus recovered is an SC5 cDNA of the invention, it can be sequenced using standard DNA sequencing techniques.

Operably cloning each cDNA so that expression of this cDNA in this clone is possible under appropriate clone culture conditions may be achieved by any conventional cloning procedure available to the skilled person. An example of cloning procedure comprises inserting each cDNA in a transfection vector under the control of a promoter suitable for the expression of this cDNA in the host cell, transfecting the host cells with this transfection vector, and cultivating the transfected host cells under conditions appropriate to their metabolism. Appropriate transfection vectors and host cells comprise virus such as Baculo virus and host cells such as insect cells (Sf9 cells), or vaccinia virus as a vector and EBV cells as host cells (see Rindis Bacher reference supra).

Such a cDNA can be used for cell transfection, and for SC5 production from the clones thus obtained. It may also be used as a probe for identifying or isolating the native SC5 mRNA.

The invention therefore also encompasses any isolated mRNA obtainable by selection among the above-mentioned mRNA population, of a mRNA which is complementary to a cDNA of the invention (e.g. via selection of a mRNA which hybridizes to the above-mentioned cDNA under stringent conditions such as described in Freeman air. et al. 1992, J. Immunol. 149: 3745). Particularly encompassed is any isolated mRNA obtainable by using an isolated cDNA of the invention as a probe so as to recover from the whole mRNA population of said cell population, the mRNA which is complementary to this extracted cDNA. Alternatively, one of ordinary skill in the art may directly sequence the cDNA that is recovered from the selected clones, and deduce from this sequence the sequence of the mRNA.

The invention also encompasses any DNA encoding an isolated mRNA according to the invention. It particularly encompasses any genomic DNA obtainable by searching a to genomic bank (such as Worldwide Website: ucsc.edu) for a genomic DNA matching with the above-mentioned SC5 cDNA.

The invention also encompasses any engineered cell in which a cDNA, a mRNA or a DNA of the invention has been transfected.

Also encompassed are SC5-specific probes and primers. Such probes and primers can be obtained by any technique available to the skilled person (e.g. selecting, as candidate sequences, portions of SC5 sequence that may be unique to SC5, comparing these candidate sequences on DNA/RNA banks with the sequences of cell receptors other than SC5, and selecting those candidate sequences which target a SC5 sequence that appears as unique after said comparison, and/or a SC5 sequence of which length appears as unique after said comparison).

Any solid support onto which is placed a cDNA, a mRNA or a genomic DNA of the invention falls within the scope of the present invention. Such solid supports notably include DNA chips, or DNA microspheres.

The invention also encompasses any isolated protein encoded by an isolated cDNA, mRNA, or DNA according to the invention.

The invention further encompasses any isolated portion of a protein of the invention, provided that this portion is still characteristic of CTCL cells by comparison with normal resting cells. It particularly encompasses any portion that is recognized by the monoclonal antibody produced by the hybridoma I-2575 at the C.N.C.M. It also encompasses any isolated portion of a protein compound of the invention, provided that this portion is capable of inducing a modulation (inhibition or stimulation) of the CD3-induced proliferation of a normal T cell, and/or is capable of inducing a modulation of the in vivo proliferation of a malignant T cell such as a CTCL cell, and/or is capable of inducing a modulation of the IL-2 production of a normal T cell or of a malignant T cell, when said portion is expressed by said cell and contacted with the mAb produced by hybridoma I-2575. It particularly encompasses any isolated portion of a protein compound of the invention, provided that this portion is a part of a molecule that is expressed in a trans-membrane location by malignant CTCL cells and that is expressed in the cytoplasm compartment by non-tumoral resting T cells.

The invention notably provides with a hank of polypeptidic fragments which is obtainable by enzymatic cleavage of the SC5 protein of the invention. Preferred enzymes comprise proteolytic enzymes such as those serine endopeptidases which cleave at the level of Tyr, Phe and Trp (e.g. alpha-chymotrypsin), and also those enzymes which cleave at the C-terminus of glutamic acid and aspartic acid (e.g. V8 protease); see e.g. Shesberadaran and Payne 1988, Proc. Natl. Acad. Sci. USA 85:1-5, of which content is herein incorporated by reference. Such a bank of SC5 polypeptidic fragments is of particular use in analysis such as mass spectrophotometry analysis: such analysis uses the characteristic separation of such a polypeptidic bank, and gives a (polypeptide) profile that is characteristic of SC5, and that can be used for SC5 detection. Such a use and such a profile are encompassed by the present application.

The invention particularly encompasses the extra-cellular, trans-membranar and intra-cytoplasmic portions of any SC5 protein compound of the invention. Determining the extra-cellular, trans-membranar and intra-cytoplasmic portions of a receptor molecule may be achieved by the skilled person according to any appropriate technique. They may be identified on the whole molecule by identification of the region which contains glycosylation sites (extra-cellular portion), of the region that is hydrophobic (trans-membrane portion), and of the region that is hydrophylic (intra-cytoplasmic region), and they may then be isolated either by cleavage or synthesis.

An alternative way to isolate the extra-cellular portion of a protein compound of the invention is to proceed as above-described for the isolation of the whole protein compound, but with an additional step of enzymatic digestion so as to cleave from the whole molecule its extra-cellular portion. Appropriate enzymes for such a cleavage includes enzymes such as V8 protease or alpha-chymotrypsin as above-mentioned.

The invention thus encompasses any isolated polypeptide compound obtainable by:
  collecting a SC5 cell source as above-described, such as e.g. PBL or total blood cells,
  if it is desired to isolate a polypeptide compound in the form it has when it is naturally expressed at the cell surface, and if the collected SC5 cell source is, or mainly comprises normal resting cells, then stimulating the CD3 pathway, e.g. via incubation with an appropriate CD3 activator (e.g. incubation with PHA at 1 microgram per ml when said SC5 source is total blood cells or PBL),
  labeling the cells with a polypeptide-specific label, such as biotin (surface labeling on whole cells),
  lysing the SC5 cell source (such as PBL or total blood cells) so as to dissociate multimeric polypeptidic complexes (and thereby recovering SC5 dissociated from the transducers and effectors naturally associated therewith) e.g. by incubating the cells in a lysis buffer comprising a drastic detergent such as Triton X-100 at 1%, and
  submitting the lysate to an enzymatic digestion enabling the cleavage of SC5 into portions, e.g. by incubating the lysate with a proteolytic enzyme such as an enzyme selected from the group consisting of V8 protease or alpha-chemotrypsin,
  submitting the lysate to immuno-precipitation with the monoclonal antibody produced by hybridoma I-2575, and
  recovering from the immuno-precipitate a polypeptide compound which bears a label.

Such recovered compounds are SC5 portions which either are the complete SC5 extra-cellular portion, or are part of such a complete SC5 extra-cellular portion, or comprise such a
  SC5 extra-cellular portion. The set of polypeptide compounds that are thus obtainable constitute a bank of SC5 "extra-cellular" portions. Such a bank, and its medical uses, such as e.g. its use for the diagnosis of a T-related disease (e.g. via mass spectrophotometry analysis), falls within the scope of the present invention.

The person of ordinary skill in the art will note that lysis and enzymatic digestion may be performed in a single step.

Labeling on whole cells is performed prior to cell lysis so as to identify SC5 portions which are extra-cellular portions, or which are part of such extra-cellular portions, or which comprise such portions.

The invention also encompasses any isolated compound which comprises a portion of a protein of the invention.

The mAb of the invention also enables the identification of the SC5 epitope onto which this mAb binds. Conventional techniques such as directed mutagenesis are appropriate (see e.g. Chang H. C. et al. 1989, J. Exp. Med. 169: 2073-2083, of which content is herein incorporated by reference).

The proteins of the invention and their portions according to the invention, and notably their extra-cellular portions, enable the production of monoclonal antibodies directed against them. An example of such monoclonal antibodies is produced by hybridoma I-2575. The monoclonal antibodies of the invention are particularly useful for the detection of SC5, for the diagnosis of T lymphomas such as CTCL, and are also useful as modulators of an undesired or inappropriate proliferation and/or activity of T cells, such as normal CD4+ and CD8+ T cells, virus-infected T cells such as HIV-infected T cells, T lymphomas such as CTCL.

The invention therefore encompasses any monoclonal antibody obtainable by:
  (i) immunizing an animal against a protein of the invention or against a portion thereof as above-defined,
  (ii) producing hybridomas from the spleen cells of this animal, and cultivating them to produce monoclonal antibodies in their culture supernatants,
  (iii) evaluating the supernatants for the presence of an antibody which is capable of binding to the protein or protein portion that has been used as an immunogen in step i., and which has at least one property selected from the group consisting of the property of:
    binding resting non-tumoral T cells mainly in their cytoplasmic compartment, and binding malignant CD4+ CTCL cells mainly at their cell surface,
    modulating the CD3 activation pathway of T cells,
    modulating IL-2 production from T cells,
    modulating the CD3-induced proliferation of T cells,
    modulating the CD3-induced in vitro proliferation of malignant T cells such as CD4+ CTCL cells, modulating the proliferation of malignant T cells such as CD4+ CTCL cells in an animal, and preferably in a human, competing with a monoclonal antibody of the invention, such as the monoclonal antibody produced by hybridoma I-2575, for binding to a protein of the invention, or to a portion thereof as above-defined, and in particular with the extra-cellular portion of such a protein, (iv) selecting and cloning hybridomas producing the desired antibody, (v) recovering the antibody from the supernatant above said clones.

Production of hybridomas may be achieved using any conventional technique. This includes removing the spleen from said animal, making a suspension of spleen cells, fusing the spleen cells with myeloma cells in the presence of a fusion promoter, diluting and cultivating the fused cells in separate wells in a medium which will not support unfused cells. The invention also encompasses any ascite isolated from said immunized animal.

For step iii., T and malignant T cells can be collected from a human using standard procedures. Alternatively, clones can be used such as the CD4+ CTCL HUT 28 cell line (ATCC TIB-161). In the case of CD4+ tumors, collection is made from the body part which will display the CD4+ tumoral cells (PBL for SS, cutaneous erythroderma for transformed MF, etc.). The above-mentioned properties can be easily assessed by the skilled person using common knowledge in the art. Examples of appropriate experimental conditions for assessing the properties mentioned in step iii. can be found in the below examples. The person of ordinary skill in the art will adjust them to the particular cells, or concentrations used. Modulation of cell proliferation herein refers to stimulation as well as inhibition of this proliferation. When CTCL cells are used, inhibition of proliferation is preferred in perspective of therapeutic application.

The mAbs of the invention are all anti-SC5 mAbs which have either diagnostic or therapeutic applications, or both. For certain applications, it may be desired to immobilize one or several of these mAb onto a support, e.g. for protein purification purposes, or for exerting the modulation property of which they are capable. The present application also encompasses any support onto which a mAb of the invention has been immobilized. Such supports notably include those appropriate for columns of chromatography by affinity (e.g. agar beads).

The present application is also directed to any fragment of a mAb of the invention (anti-SC5 fragments) selected from the group consisting of heavy chains, light chains, $V_H$, $V_L$, Fab, F(ab')2, CD1, CDR2, CDR3. It is directed to any compound, and namely to any antibody, comprising such a fragment. It notably relates to any humanized antibody comprising at least one of such fragments. Techniques for the production of humanized antibodies have been widely described in the prior art (see e.g. Farah et al. 1998, Crit. Rev. Eucaryote Gene Exp. Vol. 8 pp 321-345, of which content is incorporated herein by reference).

In particular, it relates to any compound, and notably to any antibody and humanized antibody, comprising at least one anti-SC5 fragment as herein defined and also at least one anti-CD4 fragment selected from the group consisting of heavy chains, light chains, $V_H$, $V_L$, Fab, F(ab')2, CD1, CDR2, CDR3 (see e.g. WO 94/13804 "Multivalent and multispecific binding proteins, their manufacture and use", Inventors: Holliger et al. Applicants: Cambridge Antibody Technology Ltd and Medical Research Council; see also Merchant et al. "An efficient route to human bi-specific IgG" Nat. Biotechnol. 1998 vol. 16 pp 677-681).

As previously indicated, the invention provides two molecules linked by a common general inventive concept: SC5 and p140. The SC5 is a novel molecule fully herein described. The p140 molecule has been described in the prior art as an inhibitory receptor which is expressed by sub-groups of NK cells and of CD3+ CD8+ cells from healthy (non-cancerous) patients. The present invention now demonstrates that p140 is expressed by malignant T cells, and notably by CTCL cells, and provides with a novel p140 allelic form (clone 24 in the below example 3; SEQ ID No. 1) encoding a novel protein (SEQ ID No. 2). The cDNA and amino acid sequences of this novel allelic form are as follow:

SEQ ID No. 1:
CATGTCGCTCACTGTCGTCAGCATGGCGTGCGTTGGGTTCTTCTTGCTG

CAGGGGGCCTGGCCACTCATGGGTGGTCAGGACAAACCCTTCCTGTCTG

CCCGGCCCAGCACTGTGGTGCCTCAAGGAGGACACGTGGCTCTTCAGTG

TCACTATCGTCGTGGGTTTAACAATTTCATGCTGTACAAAGAAGACAGA

AGCCACGTTCCCATCTTCCACGGCAGAATATTCCAGGAGAGCTTCATCA

TGGGCCCTGTGACCCCAGCACATGCAGGGACCTACAGATGTCGGGGTTC

ACGCCCACACTCCCTCACTGGGTGGTCGGCACCCAGCAACCCCTGGTG

ATCATGGTCACAGGAAACCACAGAAAACCTTCCCTCCTGGCCCACCCAG

GGACCCTGCTGAAATCAGGAGAGACAGTCATCCTGCAATGTTGGTCAGA

TGTCATGTTTGAGCACTTCTTTCTGCACAGAGAGGGGATCTCTGAGGAC

CCCTCACGCCTCGTTGGACAGATCCATGATGGGGTCTCCAAGGCCAACT

TCTCCATCGGTCCCTTGATGCCTGTCCTTGCAGGAACCTACAGATGTTA

TGGTTCTGTTCCTCACTCCCCCTATCAGTTGTCAGCTCCCAGTGACCCC

CTGGACATCGTGATCACAGGTCTATATGAGAAACCTTCTCTCTCAGCCC

AGCCGGGCCCCACGGTTCAGGCAGGAGAGAACGTGACCTTGTCCTGTAG

CTCCTGGAGCTCCTATGACATCTACCATCTGTCCAGGGAAGGGGAGGCC

CATGAACGTAGGCTCCGTGCAGTGCCCAAGGTCAACAGAACATTCCAGG

CAGACTTTCCTCTGGGCCCTGCCACCCACGGAGGGACCTACAGATGCTT

CGGCTCTTTCCGTGCCCTGCCCTGCGTGTGGTCAAACTCAAGTGACCCA

CTGCTTGTTTCTGTCACAGGAAACCCTTCAAGTAGTTGGCCTTCACCCA

CAGAACCAAGCTCCAAATCTGGTATCTGCAGACACCTGCATGTTCTGAT

TGGGACCTCAGTGGTCATCTTCCTCTTCATCCTCCTCCTCTTCTTTCTC

CTTTATCGCTGGTGCTCCAACAAAAAGAATGCTGCTGTAATGGACCAAG

AGCCTGCGGGGACAGAACAGTGAATAGGCAGGACTCTGATGAACAAGA

CCCTCAGGAGGTGACGTACGCACAGTTGGATCACTGCGTTTTCATACAG

AGAAAAATCAGTCGCCCTTCTCAGAGGCCCAAGACACCCCCAACAGATA

CCAGCGTGTACACGGAACTTCCAAATGCTGAGCCCAGATCCAAAGTTGT

CTCCTGCCCACGAGCACCACAGTCAGGTCTTGAGGGGGTTTTCTAGGGA

GACAACAGCCCTGTCTCAAAACC

SEQ ID No. 2:
pLMGGQDKPF LSARPSTVVP QGGHVALQCH YRRGFNNFML

YKEDRSHVPI FHGRIFQESF IMGPVTPAHA GTYRCRGSRP

HSLTGWSAPS NPLVIMVTGN HRKPSLLAHP GTLLKSGETV

ILQCWSDVMF EHFFLHREGI SEDPSRLVGQ IHDGVSKANF

SIGPLMPVLA GTYRCYGSVP HSPYQLSAPS DPLDIVITGL

YEKPSLSAQP GPTVQAGENV TLSCSSWSSY DIYHLSREGE

AHERRLRAVP KVNRTFQADF PLGPATHGGT YRCFGSFRAL

PCVWSNSSDP LLVSVTGNPS SSWPSPTEPS SKSGICRHLH

VLIGTSVVIF LFILLLFFLL YRWCSNKKNA AVMDQEPAGD

RTVNRQDSDE QDPQEVTYAQ LDHCVFIQRK ISRPSQRPKT

PPTDTSVYTE LPNAEPRSKV VSCPRAPQSG LEGVF

The DNA and amino acid sequences of the previously described p140 allelic form (clone 1.1) are as follows:

SEQ ID No. 3:
CATGTCGCTCACGTCGTCAGCATGGCGTGCGTTGGGTTCTTCTTGCTG

CAGGGGGCCTGGCCACTCATGGGTGGTCAGGACAAACCCTTCCTGTCTG

CCCGGCCCAGCACTGTGGTGCCTCGAGGAGGACACGTGGCTCTTCAGTG

TCACTATCGTCGTGGGTTTAACAATTTCATGCTGTACAAAGAAGACAGA

AGCCACGTTCCCATCTTCCACGGCAGAATATTCCAGGAGAGCTTCATCA

TGGGCCCTGTGACCCCAGCACATGCAGGGACCTACAGATGTCGGGGTTC

ACGCCCACACTCCCTCACTGGGTGGTCGGCACCCAGCAACCCGTGGTG

ATCATGGTCACAGGAAACCACAGAAAACCTTCCCTCCTGGCCCACCCAG

GGCCCCTGCTGAAATCAGGAGAGACAGTCATCCTGCAATGTTGGTCAGA

TGTCATGTTTGAGCACTTCTTTCTGCACAGAGAGGGGATCTCTGAGGAC

CCCTCACGCCTCGTTGGACAGATCCATGATGGGGTCTCCAAGGCCAACT

TCTCCATCGGTCCCTTGATGCCTGTCCTTGCAGGAACCTACAGATGTTA

TGGTTCTGTTCCTCACTCCCCCTATCAGTTGTCAGCTCCCAGTGACCCC

CTGGACATCGTGATCACAGGTCTATATGAGAAACCTTCTCTCTCAGCCC

AGCCGGGCCCCACGGTTCAGGCAGGAGAGAACGTGACCTTGTCCTGTAG

CTCCTGGAGCTCCTATGACATCTACCATCTGTCCAGGGAAGGGGAGGCC

CATGAACGTAGGCTCCGTGCAGTGCCCAAGGTCAACAGAACATTCCAGG

CAGACTTTCCTCTGGGCCCTGCCACCCACGGAGGGACCTACAGATGCTT

CGGCTCTTTCCGTGCCCTGCCCTGCGTGTGGTCAAACTCAAGTGACCCA

CTGCTTGTTTCTGTCACAGGAAACCCTTCAAGTAGTTGGCCTTCACCCA

CAGAACCAAGCTCCAAATCTGGTATCTGCAGACACCTGCATGTTCTGAT

TGGGACCTCAGTGGTCATCTTCCTCTTCATCCTCCTCCTCTTCTTTCTC

CTTTATCGCTGGTGCTCCAACAAAAAGAATGCTGCTGTAATGGACCAAG

AGCCTGCGGGGACAGAACAGTGAATAGGCAGGACTCTGATGAACAAGA

CCCTCAGGAGGTGACGTACGCACAGTTGGATCACTGCGTTTTCATACAG

AGAAAAATCAGTCGCCCTTCTCAGAGGCCCAAGACACCCCTAACAGATA

CCAGCGTGTACACGGAACTTCCAAATGCTGAGCCCAGATCCAAAGTTGT

CTCCTGCCCACGAGCACCACAGTCAGGTCTTGAGGGGGTTTTCTAGGGA

GACAACAGCCCTGTCTCAAAACC

SEQ ID No. 4:
pLMGGQDKPF LSARPSTVVP RGGHVALQCH YRRGFNNFML

YKEDRSHVPI FHGRIFQESF IMGPVTPAHA GTYRCRGSRP

HSLTGWSAPS NPVVIMVTGN HRKPSLLAHP GPLLKSGETV

ILQCWSDVMF EHFFLHREGI SEDPSRLVGQ IHDGVSKANF

SIGPLMPVLA GTYRCYGSVP HSPYQLSAPS DPLDIVITGL

YEKPSLSAQP GPTVQAGENV TLSCSSWSSY DIYHLSREGE

AHERRLRAVP KVNRTFQADF PLGPATHGGT YRCFGSFRAL

PCVWSNSSDP LLVSVTGNPS SSWPSPTEPS SKSGICRHLH

VLIGTSVVIF LFILLLFFLL YRWCSNKKNA AVMDQEPAGD

RTVNRQDSDE QDPQEVTYAQ LDHCVFIQRK ISRPSQRPKT

PLTDTSVYTE LPNAEPRSKV VSCPRAPQSG LEGVF

SEQ ID No. 1 differs from SEQ ID No. 3 in five locations.

The resulting SEQ ID No.2 differs from the p140 disclosed in prior art (SEQ ID No. 4) by four amino acid substitutions (shown in bold and underlined characters): R instead of Q in position 20, V instead of L in position 92, P instead of T in position 102, and L instead of P in position 401 (see FIG. 11).

The present application encompasses any isolated compound of which sequence is, or comprises SEQ ID No. 1 and/or SEQ ID No. 2. It also encompasses any mRNA that is complementary to SEQ ID No. 1, and any genomic DNA coding for SEQ ID No. 2.

Appropriate techniques for producing p140 proteins are available to the skilled persons. They notably include the production of cells which have been engineered so as to produce p140 proteins in their culture medium. An example of such techniques comprises inserting SEQ ID No. 1 or No. 3 in a baculo virus vector, operably transfecting an insect cell such as Sf9 cell line with this vector, recovering the p140 protein produced in the culture medium (e.g. by percolation of the culture medium through a column—e.g. a Sephadex column—which protein compounds as a function of their molecular weight, and isolating the 140 kD eluate).

Compounds capable of binding to p140 under conditions of the physiological type (in vivo conditions, or in vitro conditions mimicking the in vivo ones) have been previously described, and may be obtained by the person of ordinary skill in the art by any appropriate available technique. By "p140 binding compound", it is herein meant any compound which is capable under said conditions of the physiological type to recognize a p140 molecule as an antigen (SEQ ID No. 2 and/or SEQ ID No. 4) when it is expressed by a cell in a transmembrane receptor location (i.e. recognition of the SEQ ID No. 2 and/or No. 4 portion that is above the lipid bi-layer of said cell).

Such p140 binding compound notably comprises HLA-A11 and HLA-A3 molecules (natural p140 ligands), and notably fusion proteins such as Fc-HLA-A11 and Fc-HLA-A3 fusion proteins. p140 binding compounds also comprise p140 antiserum (obtainable by immunizing an animal such as a rabbit against p140, and by recovering the antiserum thus produced—an additional step of immuno-purification may be performed so as to increase p140 concentration in the antiserum, e.g. via percolation through a p140 column). Other p140 binding compounds comprise monoclonal antibodies directed to p140 SEQ ID No. 4, such as e.g. AZ158, Q66, Q241 described in Pende et al. 1996 (J. Exp. Med. 184: 505-518). Such anti-SEQ ID No. 4 mAbs may also recognize the new SEQ ID No. 2 as an antigen.

Any available technique for mAb production is appropriate for production of anti-p140 mAbs. An example of such a technique comprises the steps of:
 (i) immunizing an animal against p140,
 (ii) producing hybridomas from the spleen cells of this animal, and cultivating them for them to produce monoclonal antibodies in their culture supernatants,
 (iii) evaluating the supernatants for the presence of an antibody which is capable of binding to the p140 molecule that has been used as an immunogen in step i., and which is also capable of binding resting non-malignant T cells mainly in their cytoplasmic compartment, and binding malignant CD4+ CTCL cells mainly at their cell surface,
 (iv) selecting and cloning hybridomas producing the desired antibody,
 (v) recovering the antibody from the supernatant above said clones.

Preferred p140 binding compounds do also comprise an anti-CD4 entity (e.g. bi-specific mAb).

Such p140 binding compounds are useful for p140 detection on malignant T cells, such as CTCL cells, in particular CD4+ CTCL. They are thus useful for CD4+ cancer detection. They are also useful as polypeptidic vectors, as described below.

According to another aspect of the invention, there are provided polypeptidic vectors comprising at least one element selected from the group consisting of the anti-SC5 mAbs of the invention and the anti-SC5 mAb fragments of the invention. Such polypeptidic vectors are useful for molecules, such as active principle molecules, to reach activated T cells, or their vicinity (e.g. activated T cells observed in inflammatory diseases, or in virus-infected T cells, or malignant T cells such as malignant CTCL cells, and malignant CD4+ CTCL cells in particular).

It also relates to polypeptidic vectors comprising a p140 binding compound such as a mAb directed against SEQ ID No. 2 and/or SEQ ID No. 4 extra-cellular portion. Such polypeptidic vectors are useful for delivering molecules to, or in the vicinity of malignant T cells, such as notably CTCL cells, and malignant CD4+ CTCL cells in particular.

Molecules which may be usefully delivered to malignant T cells, such as CTCL cells notably comprise molecules capable of inducing cell death or apoptosis, such as a radio-element or a toxin. Such molecules also comprise any enzyme capable of transforming an antimitotic pro-drug into an active drug form, such as a carboxypeptidase. A polypeptidic vector carrying such an enzyme is then advantageously used in combination with an anti-mitotic pro-drug (such as phenol mustard pro-drug). The invention therefore also encompasses a medical kit comprising such a vector and such an anti-mitotic pro-drug.

Molecules which may be usefully delivered in the vicinity of malignant T cells such as CTCL cells notably comprise molecules capable of stimulating the immune functions of cells which are in the vicinity of malignant T cells in an effort to induce an anti-tumor effect from these neighboring cells towards said malignant T cells. Examples of such molecules notably comprise cytokines such as interferon gamma, and interleukine such as IL-2 (see e.g. Xu et al. 2000, Cancer Research 60: 4475-4484).

When a polypeptide vector of the invention is intended for targeting CD4+ cells such as CD4+ CTCL cells, then this vector advantageously further comprises an anti-CD4 entity.

The invention also encompasses any pharmaceutical composition comprising such polypeptidic vectors, and in particular any medicament comprising such polypeptidic vectors. Such medicaments are useful in the control of an inappropriate or undesired T cell. proliferation and/or functional activity (including undesired IL-2 production). They are particularly useful for the prevention, palliation, relief or therapy of an inappropriate immune activity, and notably for the prevention or inhibition of a T lymphoma such as CTCL and in particular CD4-CTCL. The use of such vectors for the manufacture of a drug intended for the prevention, palliation, relief or therapy of an inappropriate T cell proliferation and/or activity, and notably for the prevention or inhibition of a CTCL proliferation is thus also an object of the present application.

A compound which binds to SC5 under conditions of the physiological type may be used as a SC5 ligand agonist so as to stimulate the activation of SC5, the SC5 molecule being then regarded as a cell inhibitory receptor. Such anti-SC5 compounds namely comprise anti-SC5 antisera, the anti-SC5 mAb of the invention, the Fab, F(ab')2, fragments thereof, the humanized mAbs derived therefrom. When CD4+ cells are more particularly concerned, said anti-SC5 compound advantageously further comprises an anti-CD4 entity.

Anti-SC5 compounds are particularly useful for modulating an inappropriate or undesired proliferation and/or functional activity of SC5+ cells. They are thus useful for modulating the proliferation of T cells, CD45RO+ cells, CD3+ cells, CD4+ T cells, CD8+ T cells, or of virus-infected T cells (e.g. HIV-infected CD4+ T cells), or of malignant T cells such as CTCL cells and in particular CD4+ CTCL cells. They are also useful for modulating IL-2 production from T cells. When the mAb produced by the hybridoma deposited as deposit number I-2575 at the C.N.C.M. (which is a pentameric IgM) is used, this modulation goes in favor of an inhibition. It is therefore particularly appropriate for inhibition of T lymphomas such as CTCL.

The application encompasses any drug comprising, as an active principle, at least one anti-SC5 compound. Such a drug may be intended for the prevention, palliation, therapy of T lymphomas, of CTCL, of T infections such as viral (e.g. HIV) infections, of inflammatory diseases such as those of the auto-immune type (e.g. rheumatoid arthritis—e.g. spondyloarthropathis—or skin immune mediated diseases such as psoriasis, eczema, atopic dermatitis). Such a drug may also be intended for graft improvement (inhibition of graft rejection).

The invention also encompasses the use of such anti-SC5 compounds as complement recruiting agents, or as ADCC activators or stimulators.

The p140 binding compounds as defined above may also be used as complement recruiting agents, or as ADCC stimulators or activators in the prevention, palliation, relief or treatment of T lymphomas, such as CTCL and in particular CD4+ CTCL. The invention therefore encompasses the use of such p140 binding compounds in the manufacture of an anti-T lymphoma drug, of an anti-CTCL drug, of an anti-CD4+ CTCL drug, and also encompasses such drugs.

The invention also provides with a method for the assessment of the development level of a CTCL (staging): it enables to evaluate the proportion (e.g. percentage) of malignant CD4+ CTCL cells present within a certain body compartment of a patient. According to this method, the proportion of CD4+ cells expressing at their surface an element selected from the group consisting of the SC5 proteins of the invention, the SC5 portions of the invention (notably, those extracellular portions), and the p140 molecules is measured in a biological sample collected from said body compartment. The proportion of CD4+ CTCL cells that are actually present in said body compartment can be considered as substantially equal to said measured proportion. It usually falls within a ±10% range around this measured proportion.

The invention also provides with a method for CTCL diagnosis, wherein the percentage of T cells expressing an element selected from the group consisting of the SC5 proteins of the invention, the SC5 portions of the invention (notably, those extracellular portions), and the p140 molecules is measured in a biological sample collected from a patient, and is compared to the average percentage observed in non-CTCL humans (preferably in healthy humans), and in that a CTCL-positive diagnosis is decided when said measured percentage is significantly higher than said average percentage.

This CTCL diagnosis method particularly applies to those CTCL which are CD4+; in this case the measured T cell percentage is preferably a CD4+ percentage. The average standard proportion of CD4+ T cells expressing SC5 is generally in between 1-15%, usually in between 5-10% among healthy humans. When the measured percentage of SC5+ CD4+ T cells is higher than such an average percentage, then a CD4+ CTCL positive diagnosis can be concluded.

Of note is that, as far as SC5 protein or portions thereof are concerned, the methods of the invention more generally enables to evaluate the proportion of CD4+ activated T cells that are present in said body compartment. This may e.g. be useful for assessing whether a graft induces rejection reactions, and for the diagnosis and follow-up of inflammatory diseases such as those of the auto-immune type (e.g. rheumatoid arthritis such as spondyloarthropathis, skin immune mediated disease such as psoriasis, eczema, atopic dermatitis). Said biological sample may then be intra-synovial fluid. This may be also useful for the diagnosis and monitoring of non-CTCL T lymphomas (e.g. CD4+ ALL, or CD4+ T-LL).

The CTCL assessing/diagnostic methods of the invention are highly efficient for all kinds of CD4+ CTCL, and notably for transformed MF, for SS, for LP, as well as for CD30+ lymphomas. Said biological sample may e.g. then be a skin sample collected from an erythroderma (e.g.; suspicion of transformed MF), and/or a PBL or total blood sample (in order to evaluate whether a transformed MF has evolved into a more aggressive form such as SS). When the element detected at the surface of said CD4+ cells is a SC5 compound, then a (preliminary or ulterior) step of cytological observation (search for tumor-alike cytology) is preferably performed to conclude with a confidence of more than 90% to an actual CD4+ CTCL. When p140 is detected at the surface of said CD4+ cells, then no additional step is required: the simple fact of detecting p140 at the surface of CD4+ T cells directs to a positive diagnosis of CD4+ CTCL.

The methods of the invention can be implemented with any appropriate element, and notably with an element selected from the group consisting of the anti-SC5 monoclonal antibodies of the invention, the Fab, F(ab')2 fragments thereof, the humanized mAb derived therefrom, the SC5 "extra-cellular" bank of the invention (as above-defined), the SC5 cDNA, mRNA, genomic DNA of the invention, the p140 binding compounds as herein defined, the p140 DNA, the DNA comprising SEQ ID No. 1 or SEQ ID No. 3 or encoding SEQ ID No, 2 or SEQ ID No. 4.

Such an element is then used as a detection means for SC5 or p140 cell surface expression. Preferably, said detection means also comprises an anti-CD4 entity so as to detect SC5+/p140+ CD4+ cells in a one-step procedure.

When cDNA/mRNA material is used as a detection means, then CD4+ cells have to be lysed so as to detect those SC5 or p140 hybridizing mRNA which are actually present in said cells (detection of the transcripts). Such cDNA/mRNA detection means may advantageously be placed onto or into a solid support such as a DNA chip or a DNA microsphere.

When mAb material or mAb-derived material is used as a detection means, then surface expression of SC5 or p140 is detected. Any appropriate antibody-antigen technique is convenient. Examples notably comprise flow cytometry analysis.

The invention also encompasses a method for the identification of a compound which is useful in the palliation, prevention, relief or therapy of an undesired or inappropriate T cell activity, such as notably a proliferation of malignant T cells such as CTCL cells and in particular CD4+ CTCL cells. This method is characterized in that it comprises the detection of a compound that is capable of binding to a SC5 protein as above-defined, or to a SC5 polypeptide compound as above-defined, or to a p140 molecule (such as SEQ ID No. 2 and/or SEQ ID No. 4). Such compounds can be used as polypeptidic vectors as above-described. Those compounds which, in addition to binding to SC5 molecules, are also capable of aggregating these SC5 molecules at the cell surface, are preferred for stimulating SC5 inhibitory functions. An easy way to implement this identification method is to proceed with SC5 and/or p140 molecules immobilized onto a solid support such as protein A Sepharose CL-4B. Candidate compounds for implementation of the method notably comprise sera immunized against SC5 or p140.

The invention is illustrated by the examples, which are in no way intended to restrict the invention to the particular embodiments described below. The person of ordinary skill in the art will contemplate alternative embodiments, and such alternative embodiments derived from common knowledge in the art are within the scope of the invention. The skilled person will in particular appreciate that various standard immuno-techniques, and various standard molecular biology techniques are available to him (see e.g. "Antibodies: a laboratory manual" Ed Harlow, David lane, Cold Spring Harbor Laboratory 1988; Maniatis 1982, "Molecular cloning: a laboratory manual", Cold Spring Harbor, N.Y., Cold Spring Harbor Laboratory; "Current protocols in Immunology" protocols on CD-ROM, John Wiley, West Sussex, England; "Immunological techniques made easy", edited by Olivier Cochet et al., John Wiley, West Sussex, England; and the publication specifically referred to in the present application). The content of such prior art documents is herein incorporated by reference. It is also to be understood that experiments described herein in full details for one particular form of CD4+ CTCL can be directly transposed by the skilled person to any other form of CD4+ CTCL.

Figure 1B:
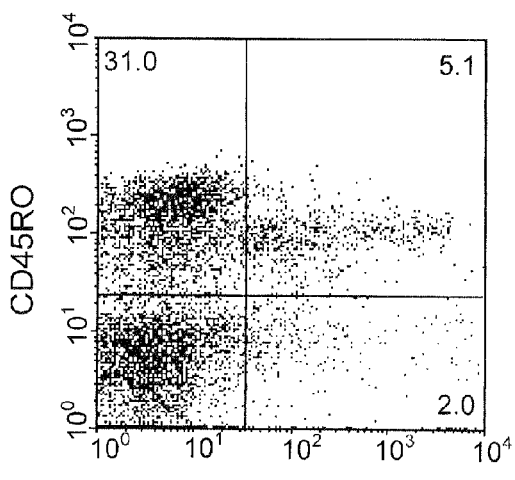
Figure 1C:
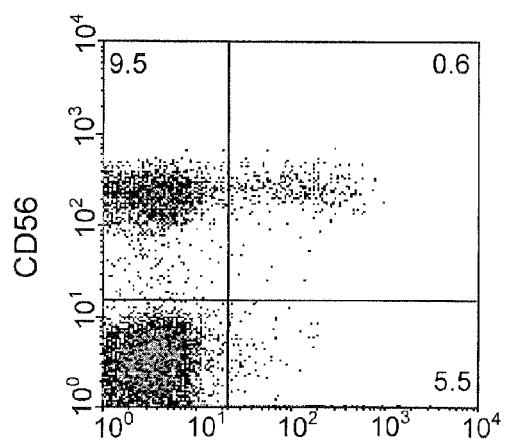

In these examples, reference is made to the following figures:

FIGS. 1A, 1B and 1C illustrate cell membrane expression of SC5 molecule on PBLs from a normal individual. PBMC from a normal individual were stained with anti-SC5 mAb (ascites (1/200)) followed by FITC-conjugated isotype specific goat anti-mouse IgM second reagent and one of the following PE-conjugated mAbs: anti-CD3 (FIG. 1A), anti-CD56 (FIG. 1C) and anti-CD45RO (FIG. 1B). The percentage of double-stained lymphocyte-gated cells is shown in the upper right quadrant (3.3 for FIG. 1A; 5.1 for FIG. 1B; 0.6 for FIG. 1C). This experiment is representative for the 10 donors studied.

Figure 2:
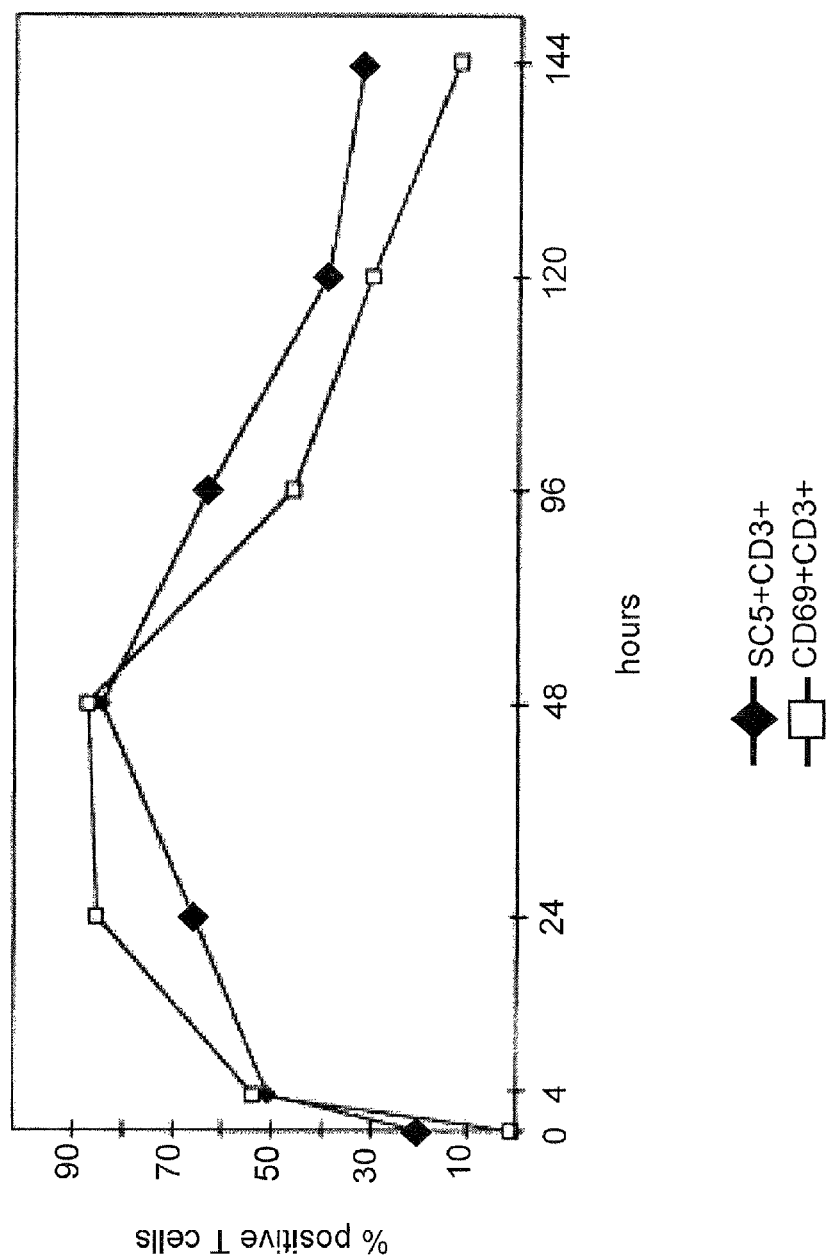

FIG. 2 illustrates cell membrane expression of SC5 molecule during activation of PBLs. PBMC were stimulated with 1 μg/mL PHA and the kinetics of SC5 and CD69 expression were studied in parallel on the CD3+ cells.

Figure 3:
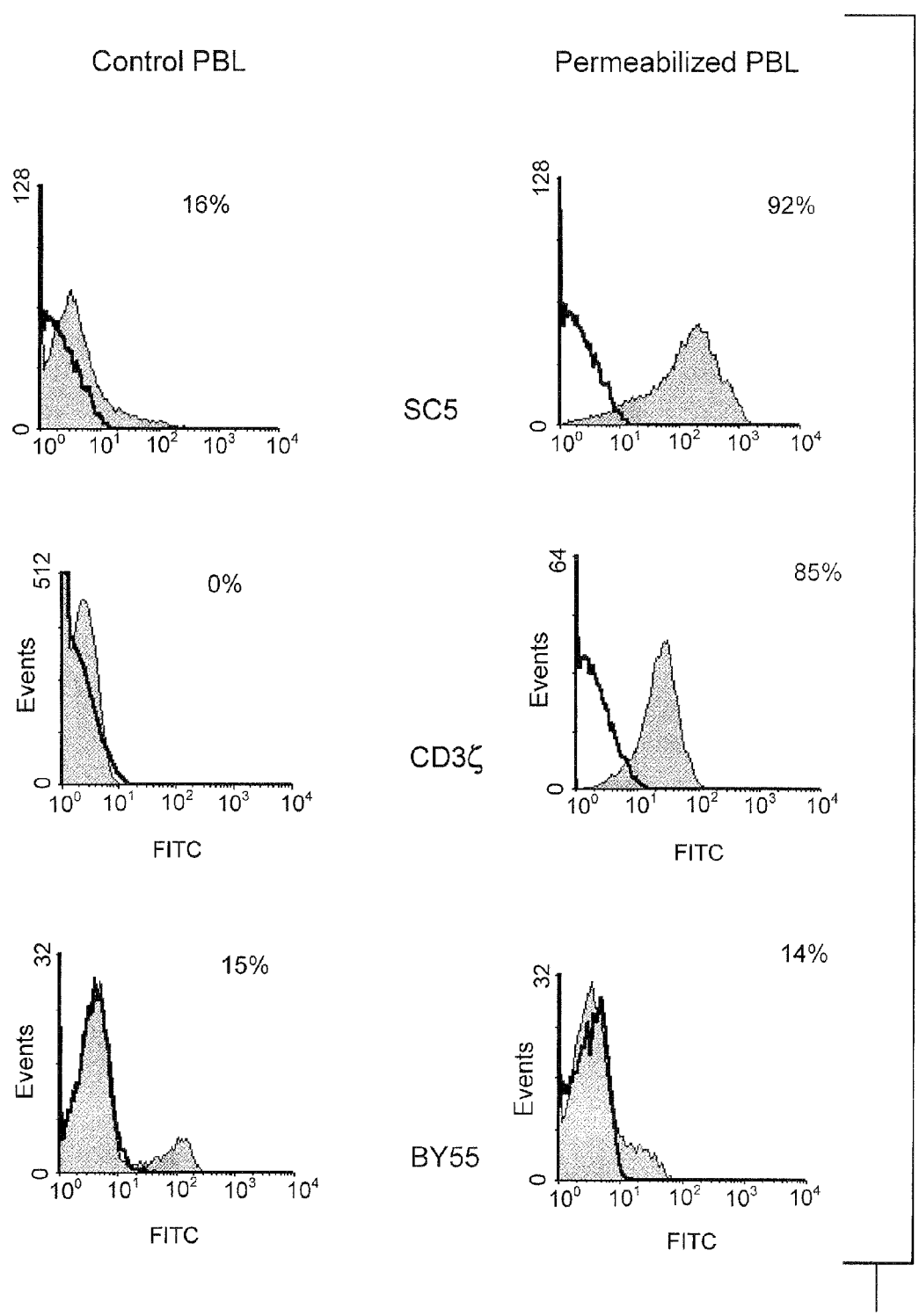

FIG. 3 illustrates intracellular localization of SC5 molecule in PBL. Anti-SC5, anti-CD3ζ chain mAb and anti-BY55 isotype-matched mAb were used for staining permeabilized and non-permeabilized gated lymphocytes from a normal donor. The shaded histograms represent the labeling obtained with the indicated mAbs compared to an irrelevant control mAb.

Figure 4:
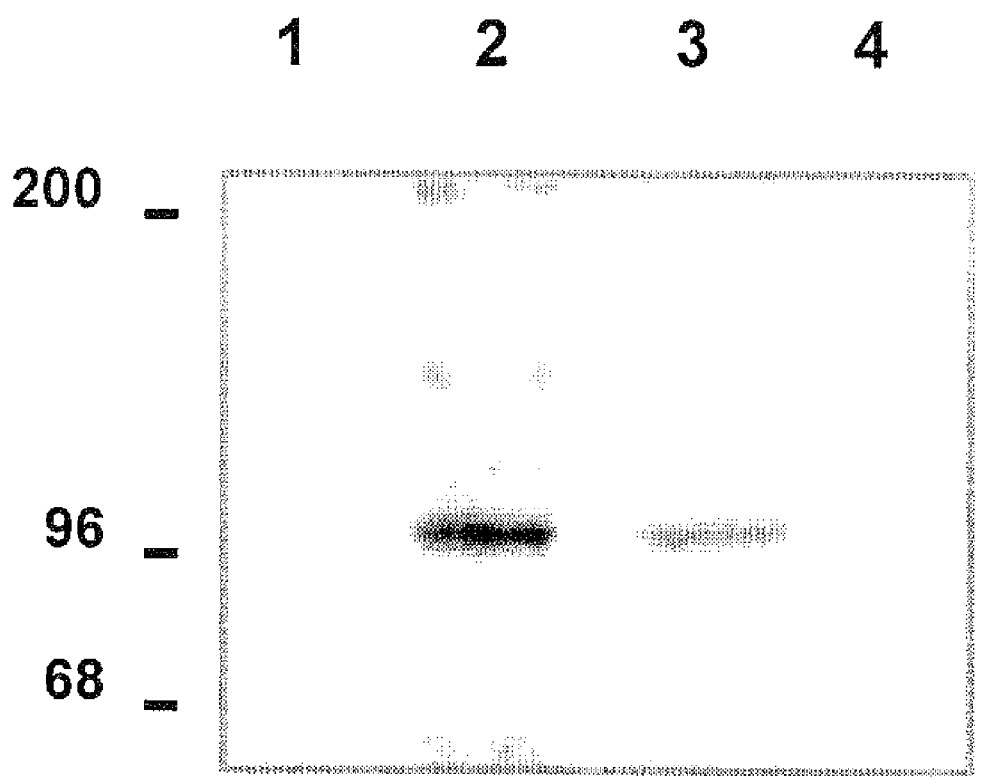

FIG. 4 illustrates biochemical analysis of SC5 molecule. DS6 T cell clone was surface labeled with biotin and 1% Triton X-100 lysates were immunoprecipitated, using anti SC5 mAb. The samples were analyzed by SDS-10%-PAGE under reducing conditions. Anti-SC5 mAb was used at two concentrations 1/200 (lanes 2) and 1/500 (lane 3). The negative control samples were precipitated with goat anti-mouse Ig alone (lane 1) and isotype-matched irrelevant mAb (lane 4). The molecular weight markers (kD), are indicated on the left.

Figure 5A:
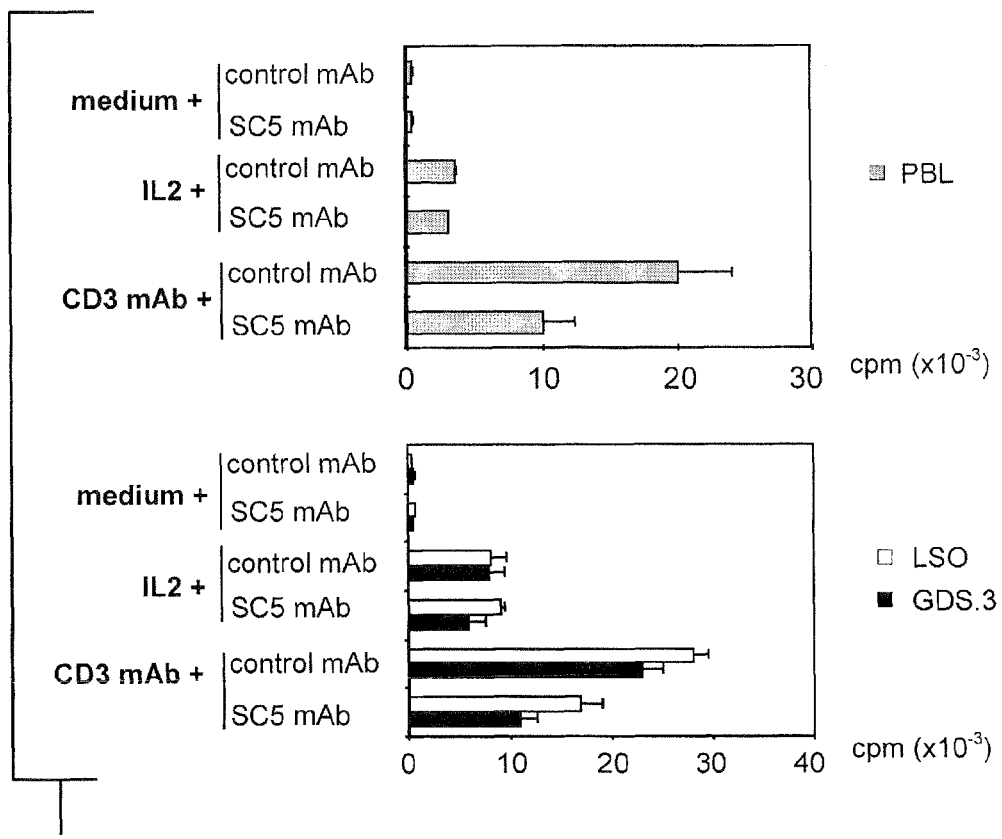

FIGS. 5A, 5B, 5C, 5D illustrate that anti-SC5 mAb modulates the anti-CD3-induced proliferation and cytokine secretion of normal T lymphocytes without affecting their cytotoxic activity:

FIG. 5A: PBL or T cell clones LSO and GDS.3 were stimulated with immobilized anti-CD3 mAb (1 μg of mAb coated per well) or with IL-2 (50 IU/ml) in the presence of anti-SC5 mAb (1:200 final dilution of ascites) or an isotype-matched irrelevant mAb. Results shown are representative of at least three separate experiments and are expressed as mean cpm±SD of triplicate wells.

Figure 5B:
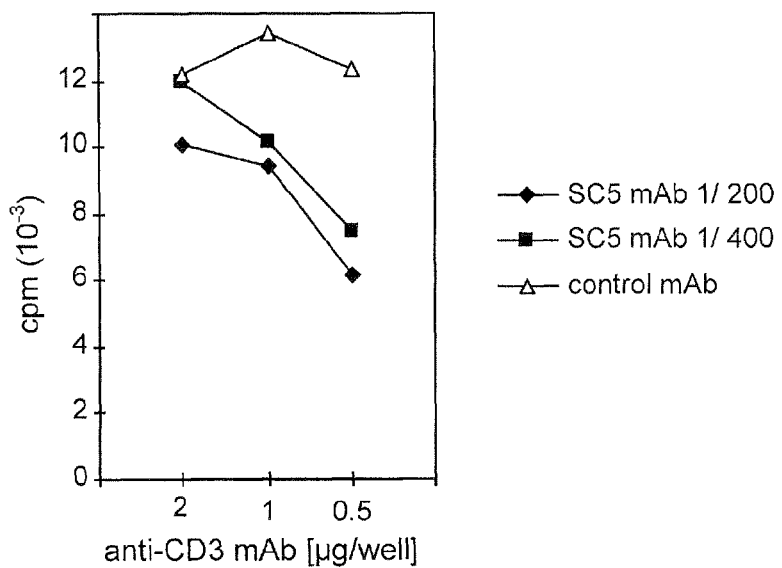

FIG. 5B: GDS.3 CD4+ T cell clone was stimulated with the indicated concentrations of pre-coated anti-CD3 mAb in the presence of different concentrations of anti-SC5 mAb.

Figure 5C:
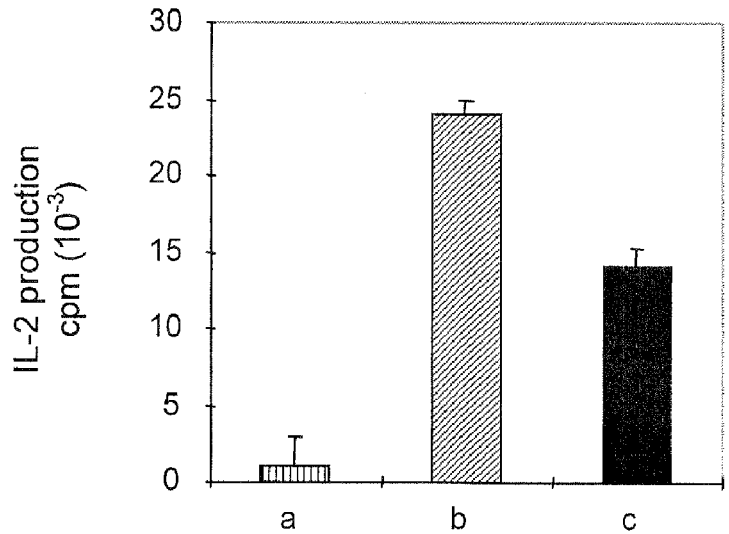

FIG. 5C: IL-2 secretion in the supernatant of anti-CD3-stimulated PBL, in the presence of anti-SC5 or control mAb, was assessed by measuring the proliferation of an IL-2 dependant T cell clone in the presence of: medium alone (a), supernatant from PBL/anti-CD3+control mAb (b), supernatant from PBL/anti-CD3+anti-SC5 mAb (c). Data represent the mean values ±SD of triplicate determinations of one out of three representative experiments.

Figure 5D:
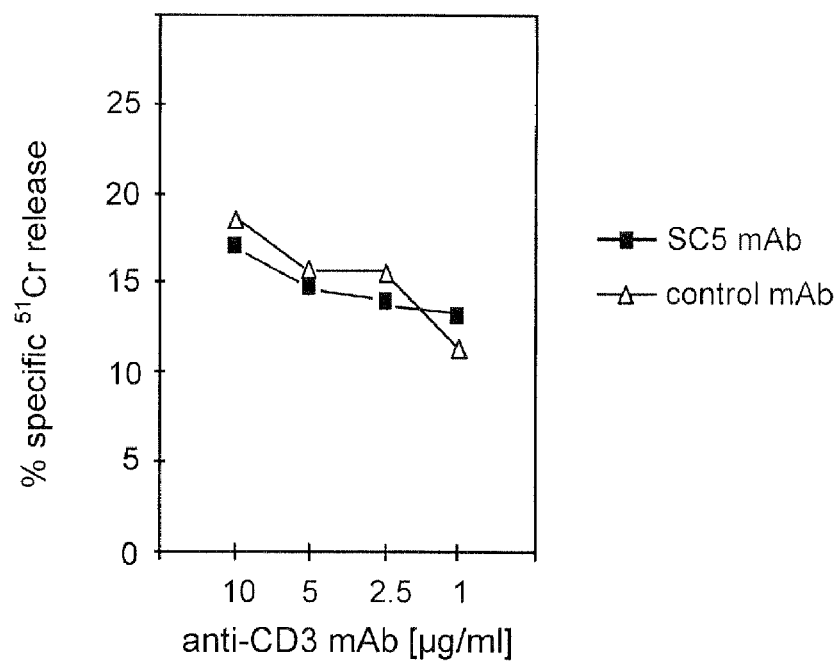

FIG. 5D: JF1, a cytotoxic CD8+ cell clone was incubated with anti-SC5 mAb (1/200 final dilution of ascites) or with an isotype matched control mAb before the coculture with the FcγR+ murine tumor cells P815 at an E/T ratio of 5/1. Target cells were preincubated with the indicated final concentrations of anti-CD3 mAb. Results are expressed as mean of triplicate wells.

Figure 6A:
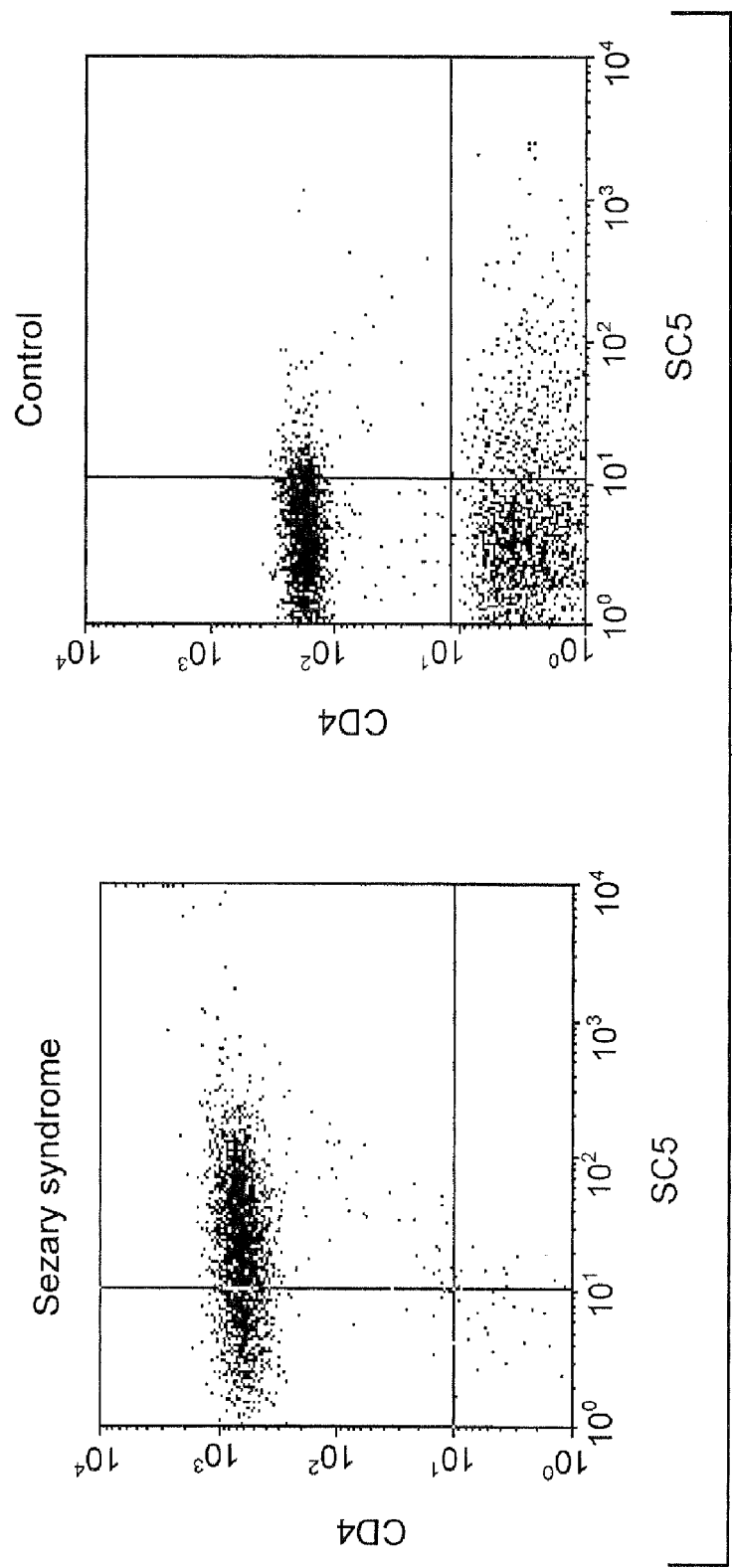
Figure 6B:
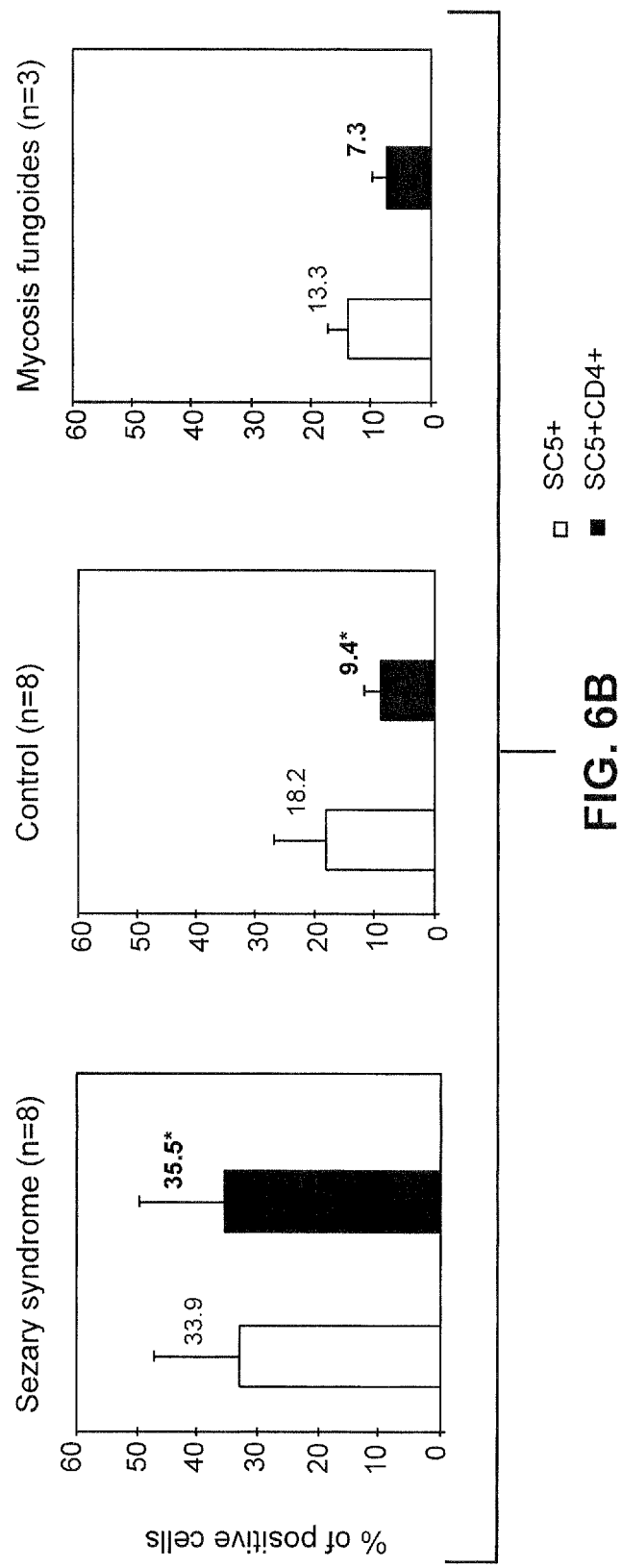

FIGS. 6A, 6B illustrate cell membrane expression of SC5 molecule on PBL from CTCL patients. Cells from peripheral blood of 8 patients with Sézary syndrome, 3 patients with Mycosis fungoides and 8 healthy donors were analysed by two-color fluorescence for the expression of SC5 molecule by CD4+ lymphocytes.

FIG. 6A: co-expression of SC5 and CD4 molecules in PBL from a patient with Sézary syndrome in comparison to a normal individual.

FIG. 6B: histograms showing the mean values of SC5 expression in the 3 indicated groups. Statistically significant differences between SS patients and 2 other groups are marked, (Mann-Witney U test, p<0.001).

Figure 7C:
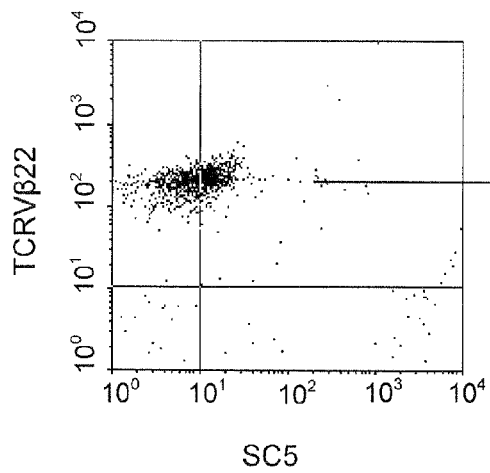
Figure 7C:
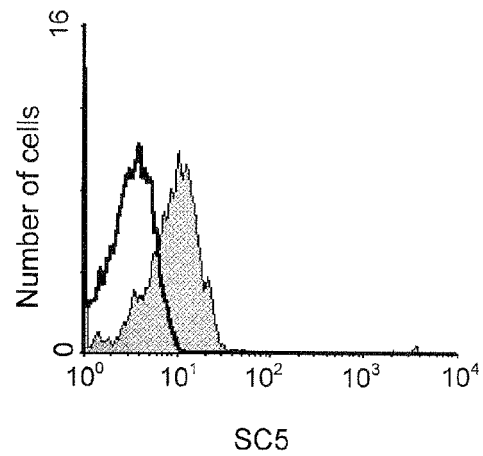
Figure 7C:
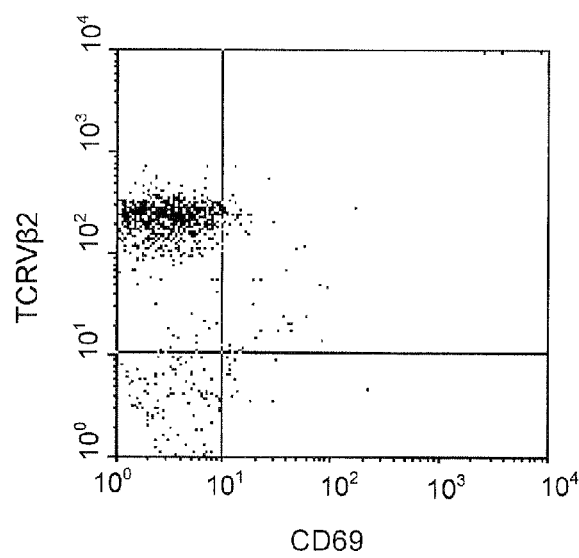

FIGS. 7A, 7B, 7C illustrate surface membrane expression on malignant cell from Sézary syndrome patient.

FIG. 7A: two-color immunofluorescence analysis of PBMC from SS patient with a circulating TCRVβ22+ malignant T cell clone. Cells were stained with anti-SC5 mAb followed by PE-conjugated isotype specific goat anti-mouse IgM and FITC-conjugated anti-TCRVβ22 mAb.

FIG. 7B: anti-SC5-mAb labeled weakly (shaded histogram) the TCRVβ22-positive malignant cells.

FIG. 7C: cells from the same patient stained with PE-conjugated anti-CD69 mAb and FITC-conjugated anti-TCRVβ22 mAb.

Figure 8:
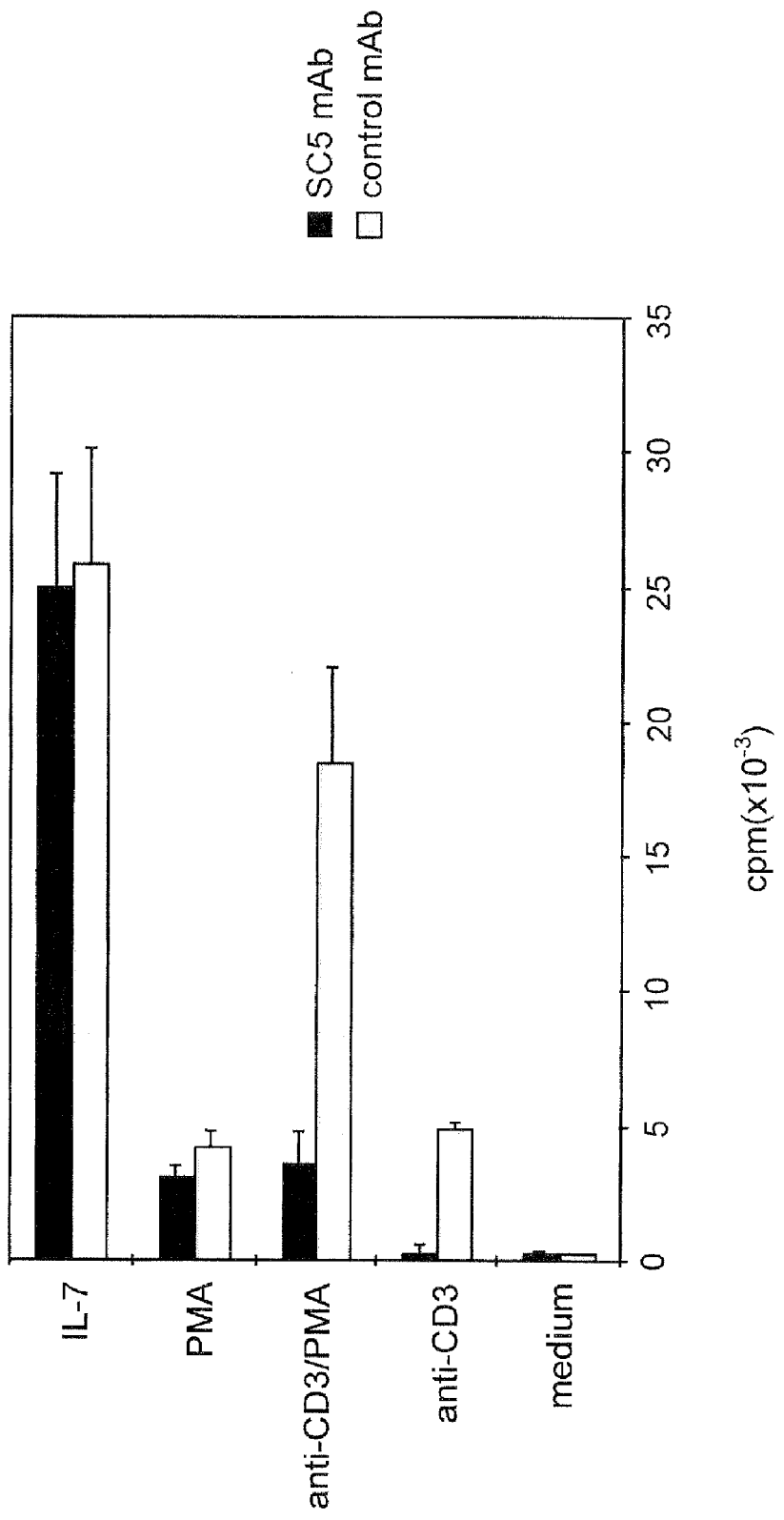

FIG. 8 illustrates the modulation of anti-CD3-induced proliferation of CTCL malignant cell line by anti-SC5 mAb. Pno cell line was stimulated with IL-7 (10 ng/mL), PMA alone (2 ng/mL), immobilized anti-CD3 mAb or a combination of PMA/anti-CD3 mAb. SC5 mAb or an isotype-matched irrelevant mAb (1:200 final dilution of ascites) was added at the start of cultures. Results shown are representative of four separate experiments and are expressed as mean cpm±SD of triplicate wells.

Figure 9A:
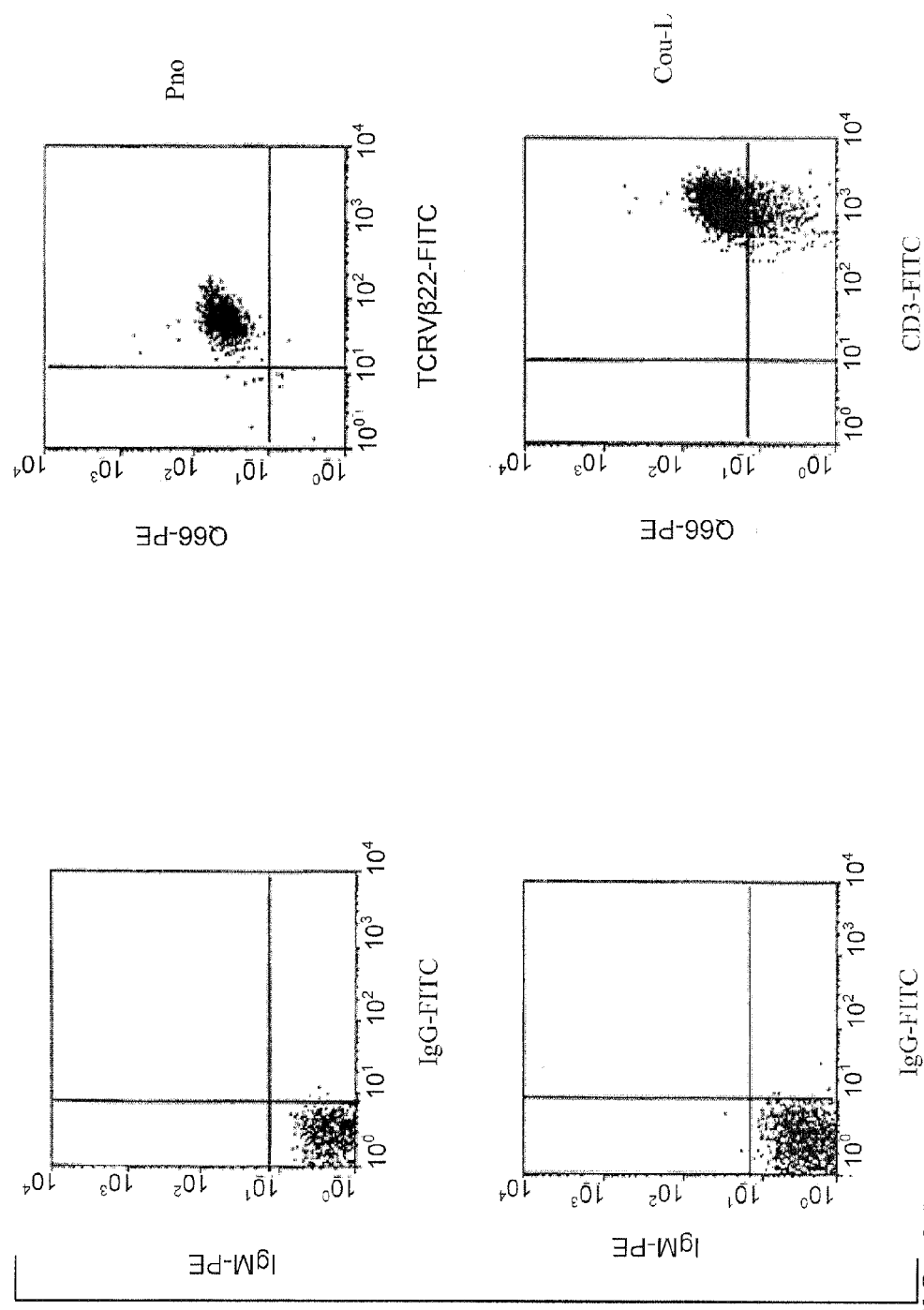
Figure 9B:
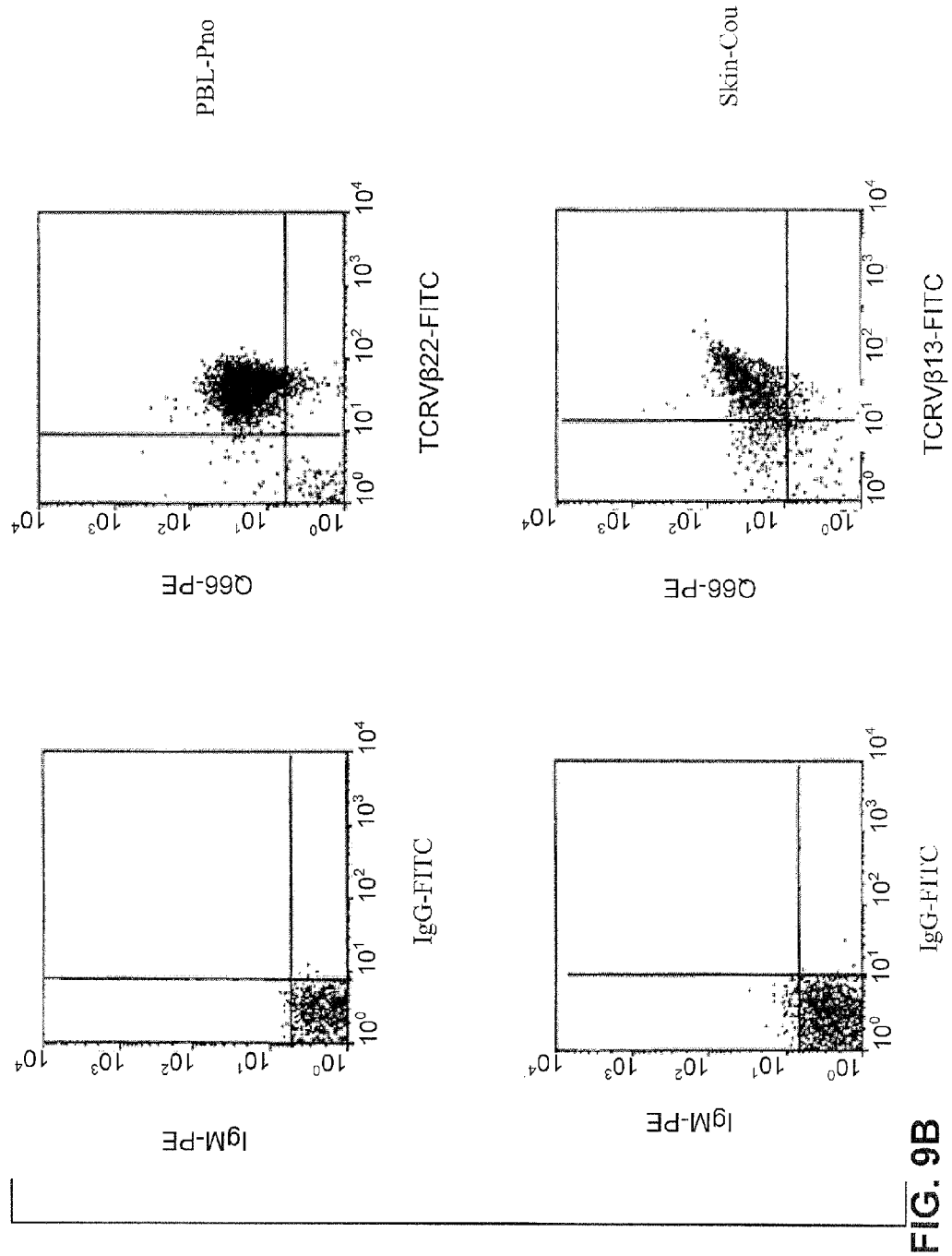

FIGS. 9A, 9B illustrate the detection of p140/KIR molecules on CTCL cell lines (FIG. 9A) and on fresh tumor lymphocytes (FIG. 9B). Double immunostaining flow cytometric analysis was performed as described in Bagot et al. 1998 (Blood 91:4331-4341) and in Poszepczynska et al. 2000 (Blood 96: 1056-1063).

Figure 10:
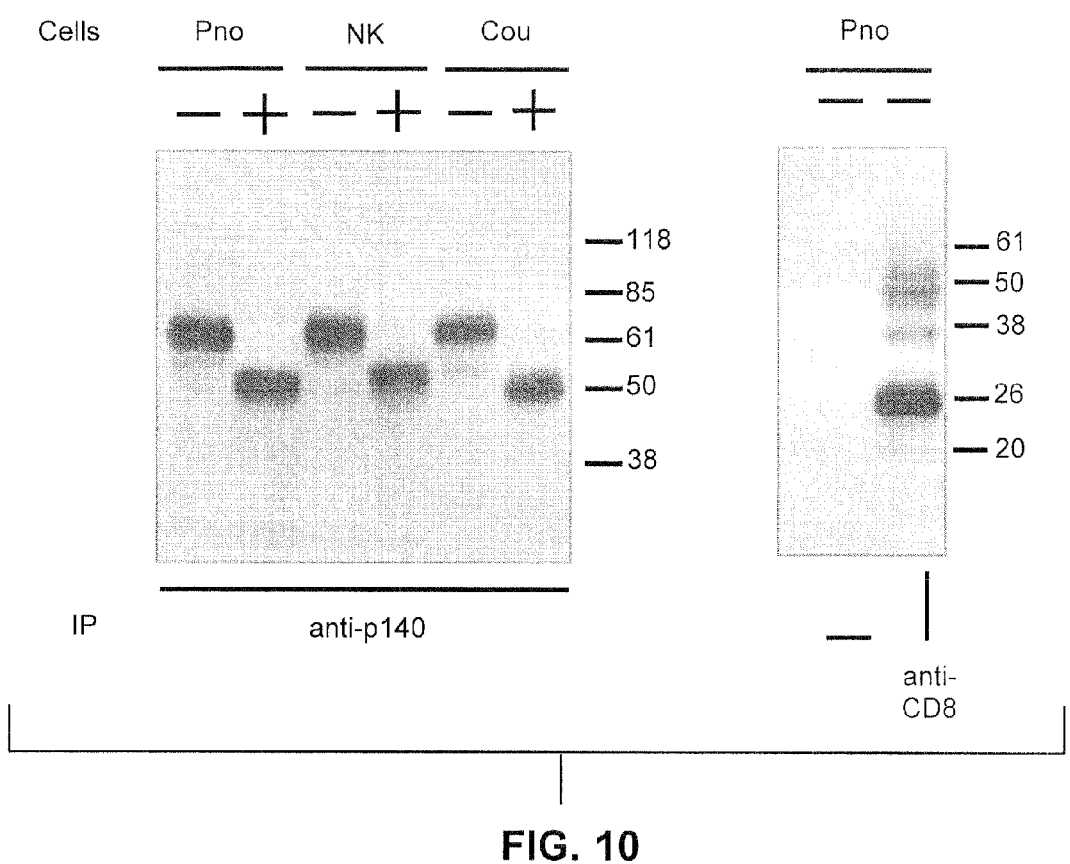

FIG. 10 illustrates the biochemical analysis of p140 molecules: the NK clone AM61 (p140+/p70−), derived from a healthy donor, and the cell lines Pno and Cou-L were surface labeled with biotin and immunoprecipitated with anti-p140 and anti-CD8 mAbs. Samples were treated (+) or not (−) with N-glycosidase F and analyzed in an 8% (left panel) or 11% (right panel) SDS-PAGE under reducing conditions. Sepharose Protein-A alone represents the negative control. Molecular weight markers (kD) are indicated on the right.

FIG. 11 shows the amino acid sequence alignment of KIR3D cl. 24 (SEQ ID No. 2) and cl. 1.1 (SEQ ID No. 4) encoded proteins. Amino acids corresponding to the signal peptide are in small case letters, while transmembrane region is underlined in the consensus sequence. Amino acids identical to the consensus sequence are indicated by dots.

EXAMPLE 1

SC5 Isolation, SC5 Biochemical and Functional Characterization, Production of Anti-SC5 mAbs T lymphocyte immune responses are regulated by functional cell surface molecules providing positive signals that lead to the expansion of antigen-specific clones, and negative signals which prevent excessive stimulation or responsiveness to self antigens. The activation of resting T lymphocytes requires two independent signals. The signal provided by the engagement of T-cell receptor (TCR) must be accompanied by a second positive signal in order to result in optimal T cell response. CD28 is considered as the major co-stimulatory receptor inducing T lymphocyte activation and IL-2 synthesis and preventing cell-death. Recent studies demonstrated that CD3/TCR stimulation leads to a redistribution of the detergent-insoluble glycolipid-enriched membrane fraction (DIG) or raft, which results in the aggregation of TCR/CD3 and DIG-associated signal-transducing molecules. CD28 was reported to enhance raft redistribution to the site of TCR engagement. Further, a series of other molecules may provide co-stimulatory signals to T cells, acting at different time points, affecting particular subsets or promoting distinct effector functions. Negative regulation of T lymphocyte responses can be mediated by CD152-induced signals or by apoptosis through the members of TNF receptor superfamily. Recently, a novel type of negative regulation has been reported for subsets of NK cells and CD8+ T lymphocytes (Lan998, Annu, Rev. Immunol. 16: 359-393). The immunoglobulin-like (KIRs) or C-type lectin structures responsible for these signals prevent unwanted effector functions such as activation of CTL activity or cytokine production.

We now describe a novel 96 kD transmembrane receptor, SC5, which delineates a minor subset of peripheral blood lymphocytes in normal individuals. Anti-SC5 mAb stained mainly CD45RO+ lymphocytes, from both CD8 and CD4 subsets, as well as NK lineage cells. We found that SC5 was predominantly located in the intracellular compartment of resting T lymphocytes and its surface membrane expression increased rapidly after cell activation. SC5 molecule engagement inhibited the anti-CD3 mAb-induced proliferation of resting T lymphocytes or T cell clones, whereas it had no effect on the cytokine-induced proliferation of these cells. At the same time, the effector cytotoxic activity mediated by CD8+ T cell clones was not altered by anti-SC5 mAb. Further on, we observed that the percentage of SC5+CD4+ circulating lymphocytes was significantly increased in Sézary syndrome (SS) patients as compared to peripheral blood lymphocytes of normal individuals, Importantly, we were able to clearly demonstrate that Sézary cells express SC5 molecules. In addition, we found that ligation of SC5 molecules in a cutaneous T cell lymphoma (CTCL) cell line resulted in a strong inhibition of the malignant cell proliferation induced by anti-CD3 mAbs. Thus, SC5 molecule expression can serve to detect the presence of circulating malignant CD4+ cells in SS patients. Moreover, the identification of a cell surface molecule providing negative signals upon ligation constitutes a new tool to investigate the mechanisms of pathological T cell growth and could be used to prevent it.

Material and Methods

Production of Anti-SC5 mAb

SC5 mAb was obtained by immunizing 6 wk old Balb/c mice with the NK cell line Ytindi, using an established protocol (David et al. 1990; J. Immunol. 144: 1-6). Hybridoma supernatants were screened for selective reactivity with the immunizing cell line and a CTCL cell line termed Pno (Poszcepczynska et al. 2000; Blood 96: 1056-1063) by indirect immunofluorescence and flow cytometry. Pno cell line derives from CTCL cells from a patient which had a CD3+ Vβ22+ CD4+ CD8αα+ CD25-phenotype, and which proliferates in response to IL-7 and to anti-CD3 mAb stimulation. Any CTCL cell line is appropriate for this screening. Examples of other CTCL cell lines include the HUT78 cell line (ATCC TIB-161). The reactive supernatants were further tested for their reactivity with peripheral blood lymphocytes (PBL). A hybridoma supernatant was selected for its reactivity with both tumoral cell lines and with a minor PBL subpopulation. The hybridoma was cloned twice and cloned hybridomas were passaged into pristane-primed Balb/c mice to produce ascites. The antibody isotype was determined as IgM and termed anti-SC5 mAb. The ascites was dialysed against PBS, sterilized by ultrafiltration and further utilized at final dilution 1/200. This hybridoma has been deposited on Oct. 30, 2000 at the C.N.C.M. (Collection Nationale de Microorganismes, Institut Pasteur, 25, rue du Docteur Roux, F-75724 Paris Cedex 15, France) in accordance with the Budapest Treaty; the C.N.C.M. deposit number is I-2575. In this example, "anti-SC5 mAb" refers to the mAb produced by hybridoma I-2575.

Patients

After informed consent and approval by an ethic committee (CCPPRB, Hôpital Henri Mondor, Creteil, France), we obtained blood samples from eleven patients with CTCL. Eight patients had a Sézary syndrome with 10 to 80% circulating CD3+, CD4+, CD8− Sézary cells, whereas three patients had a transformed mycosis fungoides (MF) and presented with disseminated skin tumors with a CD3+, CD4+, CD8− phenotype. All patients were not previously treated with chemotherapy.

Cells and Cell Lines

Peripheral blood mononuclear cells (PBMC) were isolated by the technique of Ficoll-Isopaque (Pharmacia fine Chemicals, Piscataway, N.J.) density gradient centrifugation. Human T cell clones GDS.3 (CD3+TCRαβ+CD4+CD8−), DS6 (CD3+TCRγδ+CD4−CD8−), LSO (CD3+TCRγδ6+ CD4−CD8−) and JF1 (CD3+TCRαβ+CD4−CD8+), described in Bensussan et al. 1984 (J. Exp. Med. 159: 947-952) and Yssel et al 1984. (J. Immunol. Methods 72: 219), were fed each 8 days with irradiated allogenic PBMC in culture medium consisting of RPMI 1640 (GIBCO, Paisley, UK), 2 mmol/L L-glutamine, penicillin (100 U/ml), streptomycin (100 mg/ml), 10% heat-inactivated human serum, 50 IU/ml recombinant interleukin-2 (rIL-2, Sanofi Synthélabo, Labège, France) and 1 µg/ml phytohemagglutinin (PHA), (Wellcome, Beckenham, UK). Functional studies were performed at day 7 after the feeding. Standard human leukemic cell lines were mycoplasma-free and maintained in logarithmic growth in complete RPMI medium supplemented with 10% fetal calf serum (FCS) and antibiotics. The human CTCL cell clone, Pno, was established from peripheral blood of a Sézary patient and maintained in culture as previously described (Poszcepczynska et al. 2000; see supra). Pno cell line has a CD3+Vβ22+CD4+CD8αα+CD25− phenotype and proliferates in response to IL-7 and to anti-CD3 mAb stimulation. Other CTCL cell lines include the HUT78 cell line (ATCC TIB-161).

Monoclonal Antibodies and Flow Cytometry Studies

Indirect immuno-fluorescent staining was performed with hybridoma supernatants or ascites fluid using FITC-conjugated goat anti-mouse Ig from Caltag laboratories (San. Francisco, Calif.). For two-color analysis the immuno-fluorescent staining was performed by incubating $3 \times 10^5$ cells with anti-SC5 mAb for 30 min at 4° C. Cells were then washed and incubated with FITC-conjugated goat anti-mouse IgM (Caltag laboratories) followed by a second PE-, ECD- or TRI-conjugated specific mAb of IgG isotype. Stained cells were analyzed using a single argon flow cytometer analyser (Epics XL, Bekman-Coulter, Miami, Fla.) as described in Schiavon. V. et al. 1999; Tissue Antigens 53: 23-32. For intracellular labeling, cells were fixed in PBS 4% p-formaldehyde for 20 min at 4° C., washed, and then permeabilized with staining buffer containing 0.1% saponin. Conjugated anti-CD3, anti-CD4, anti-CD8, anti-CD45RO, anti-CD69, and anti-TCRVβ22 mAbs were purchased from Immunotech (Marseille, France).

Other mAbs are available from Beckman Coulter (see Cell Analysis 2000 catalogue): anti-CD3 (PE) Cell Analysis 2000 catalogue reference IM1282; purified anti-CD3 Cell Analysis 2000 catalogue reference IM0178; Cell Analysis 2000 catalogue reference anti-CD4 IM0449; anti-CD8 Cell Analysis 2000 catalogue reference IM0452; anti-CD45RO Cell Analysis 2000 catalogue reference IM1307; anti-CD69 Cell Analysis 2000 catalogue reference IM1943; anti-CD94 Cell Analysis 2000 catalogue reference IM2276; anti-CD158a Cell Analysis 2000 catalogue reference IM2277; anti-CD158b Cell Analysis 2000 catalogue reference IM2278; anti-NKG2a Cell Analysis 2000 catalogue reference IM3291; anti-BY55 Cell Analysis 2000 catalogue reference IM2745.

Immunoprecipitation of Biotinylated Surface Molecules.

$2 \times 10^7$ cells were washed twice in PBS and surface-labeled with Sulfo-NHS-LC biotin (Pierce Europe, Interchim, Montlucon, France) (2 mg/mL in PBS) for 20 min at 4° C. After quenching for 20 min with RPMI 1640, cells were washed twice in PBS and re-suspended in lysis buffer (20 mM Tris-HCl pH 7.5, 150 mM NaCl, 1% Triton X-100, 1 mM Na Vanadate, 10 mM NaF, 1 mM PMSF, 1 μg/mL aprotinin, and 1 μg/mL leupeptin) for 1 h to at 4° C. Postnuclear supernatant was then incubated for 2 h at 4° C. in a 96-well plate (Maxisorp Nunc immuno-plate) pre-coated with goat anti-mouse IgG+IgM (Caltag laboratories) followed by anti-SC5 mAb or anti-TCRβ (anti-TCRβ C305 isotype matched mAb, Cell Analysis 2000 catalogue reference IM1466; anti-TCRV-beta22, Cell Analysis 2000 catalogue reference IM2051; anti-TCRzeta, Cell Analysis 2000 catalogue reference IM3169; all from Beckman Coulter). Immuno-precipitates were washed 4 times with washing buffer (20 mM Tris-HCl pH 7.5, 150 mM NaCl, 0.1% Triton X-100, 1 mM Na Vanadate, 10 mM NaF, 1 mM PMSF) and precipitated proteins were subjected to SDS-PAGE. Western blot analysis was performed using streptavidin-peroxidase (Immunotech) and the ECL detection system according to manufacturers' recommendations (Amersham Pharmacia, Orsay, France).

Proliferation Assays

For lymphocyte activation, PBMC were cultured in medium containing 15% human serum in the presence of 1 μg/ml PHA (Wellcome, Beckenham, UK). For proliferation assays, $5 \times 10^4$ cells were cultured in triplicates in 96-well round-bottomed plates (Greiner, Nürtingen, Germany) in a final volume of 0.2 ml culture medium. When needed, the plates were pre-coated with anti-CD3 mAb at the indicated concentrations as previously described (Poszcepczynska et al. 2000, see supra). For stimulation of CTCL cell line Pno, pre-coated anti-CD3 mAb was used in combination with 2 ng/ml phorbol 12 β-myristate 13 α-acetate (PMA, Sigma Biochemicals). Cells were cultured for 4 days and were pulsed with 1 μCi of $^3$H[TdR] during the last 8-16 h of culture. $^3$H[TdR] incorporation was measured in a liquid scintillation counter (Topcount; Packard Instrument Co, Meriden, Conn.). For the determination of IL-2 production, $10^5$ PBL were stimulated with immobilized anti-CD3 mAb in the presence of anti-SC5 or control mAb. After 32 hours of culture, 100 μL of supernatant was added to $10^5$ cells from an IL-2-dependent T cell clone.

CD3-Induced Redirected Cytotoxicity Assays

The redirected cytotoxicity assay was carried out as described in Le Cleach et al. 2000, Clin. Exp. Immunol. 119: 225-230. The target murine mastocytoma P815 tumor cells were loaded with 100 μl $^{51}$Cr (2.5 mCi/mL) for 90 min at 37° C., washed and incubated with anti-CD3 mAb for 15 min at room temperature. Effector cells were likewise pre-incubated with anti-SC5 mAb (1:200 final dilution of ascites) and added to target cells in ratio 5:1, in a final volume of 150 μl in 96 well V-bottomed microtiter plates for 4 h. After centrifugation 100 μl aliquots were counted in a gamma-counter to determine $^{51}$Cr release. The spontaneous release was always less than 20% from the maximum release (target cells with 1% NP40). Percentage of specific $^{51}$Cr release was calculated as described in David et al. 1987, J. Immunol. 138: 2831-2836.

Statistical Analysis

Statistical analysis of the results was performed with Statistica software vers. 5.0 (StatSoft, Los Angeles, Calif.). Significant differences between SC5 expression in patients and control group were evaluated by the Mann-Whitney U test, and the correlation between the percentage of SC5+CD4+ cells and the percentage of malignant cells in patients peripheral blood was evaluated by the Spearman Rank Order Correlations test.

Results

The results herein reported have been obtained with the CTCL cell line Pno, and with CTCL cells collected from patients. Equivalent experiments and results can be performed and obtained with any CTCL cell line, such as e.g. HUT 78 (ATCC TIB-161).

Expression of SC5 Molecules in Normal Resting and Activated Peripheral Blood Lymphocytes Monoclonal antibodies raised against the functional tumor cell line Ytindi were analyzed for their simultaneous reactivity with the CTCL cell line Pno (Poszcepczynska et al. 2000, see supra) and normal peripheral blood T cells. The SC5-specific mAb, of IgM isotype, stained both the immunizing and CTCL cell lines. Among peripheral blood lymphocytes, anti-SC5 mAb delineated a small sub-population (see FIG. 1A, 1B, 1C). The SC5 mAb reactive molecule was expressed by a variable percentage of CD3+ T cells, never exceeding 20% (mean=10.5%, SD±5.6). Both CD4+ and CD8+ lymphocytes were stained by anti-SC5 mAb. A sub-population of peripheral blood CD56+ NK cells was also reactive with anti-SC5 mAb, though with more important inter-individual variations (mean=19.4%, SD±11.4); see the below Table 1.

TABLE 1 expression of SC5 in peripheral blood lymphocyte sub-populations

| Cell population | N tested | mean (%) | SD |
|---|---|---|---|
| Total Ly | 15 | 14.1 | 6.8 |
| CD3+ Ly | 10 | 10.5 | 5.6 |
| CD4+ Ly | 8 | 9.4 | 5.1 |
| CD8+ Ly | 8 | 14.8 | 5.1 |
| CD56+ Ly | 10 | 19.4 | 11.4 |

A representative example of SC5 co-expression with CD3 or CD56 molecules on gated lymphocytes from PBL of normal donors is shown in FIG. 1A. It should be noted that most SC5+ lymphocytes belonged to the activation/memory pool, as demonstrated in FIG. 1B. Over 70% of the SC5-positive cells co-expressed CD45RO.

As SC5 molecule expression was detected in all IL-2 dependent T lymphocyte clones tested, we verified whether its cell surface expression was induced during T lymphocyte activation. We found that stimulation of PBL with PHA promptly increased the expression of SC5 on CD3+ lymphocytes. Both the percentage of SC5+ T cells and the level of SC5 expression rose very rapidly after stimulation (see FIG. 2). As early as 4 hours after stimulation with PHA, the percentage of SC5+CD3+ cells increased two to threefold and reached a maximum after 24 to 48 hours. In the course of 5 to 7 days of in vitro stimulation SC5 expression returned to the basal level. In parallel we studied the expression of the very early activation antigen CD69 and we observed similar kinetic profiles of CD69 and SC5 on CD3+ lymphocytes. It should be noted, that unlike CD69 molecules, low levels of SC5 were already present on circulating PBL before stimulation (FIG. 2).

Activation-induced antigen expression results either from de novo protein synthesis or cell surface export of preexisting intracellular molecules. Therefore, we studied the expression of SC5 in non-activated permeabilized PBL. As shown in FIG. 3, anti-SC5 mAb stained over 90% of permeabilized lymphocytes vs. 16% of the same non-permeabilized cells. The specificity of anti-SC5 mAb staining was confirmed by using the isotype-matched mAb BY55 which detects a GPI-anchored cell surface structure expressed by a subset of circulating lymphocytes (see Agrawal et al. 1999, J. Immunol. 162: 1223-1226). A comparable percentage of BY55+ cells was found in permeabilized and non-permeabilized lymphocytes. As a positive control for the detection of an intracellular epitope, we used an anti-CD3ζ chain mAb which only labeled permeabilized T lymphocytes. Thus, the surface expression of SC5 is dynamically regulated by the activation status of cells and its induction during T cell activation is due to the enhanced transport of the molecule from an intracellular pool to the surface membrane.

Biochemical Characterization of SC5 Antigen

In order to characterize the molecular weight of the structure identified by anti-SC5 mAb, an IL-2 dependent TCRγδ+ clone, termed DS6, was surface labeled with biotin and the cell lysates were immuno-precipitated with either anti-SC5 mAb or an isotype-matched anti-TCRβ mAb (as negative control). Anti-SC5 mAb recognized a single molecule with apparent molecular weight of 96 kD under reducing conditions (see FIG. 4). As tumor cell lines (the immunizing Ytindi cells) are often characterized by aberrant expression of carbohydrate epitopes (20, 22), we studied the reactivity of anti-SC5 mAb with the SC5+ NK cell line NK3.3 and with the CTCL cell line HUT78 (ATCC TIB-161) after treatment with neuraminidase or sodium periodate in concentrations destroying known sialylated epitopes (digestion of CD75 epitope on Raji cells was used as a positive control). Expression of SC5 was not affected by neuraminidase or sodium periodate treatment. Thus, we excluded a possible carbohydrate nature of the epitope.

Inhibition of the Anti-CD3 mAb-Induced T Lymphocyte Proliferation by Anti-SC5 mAb In order to examine the possible function of SC5 molecule in normal T cells, we studied the effect of anti-SC5 mAb alone or during the proliferative responses induced by immobilized anti-CD3 mAb. We found that anti-SC5 mAb alone or in combination with PMA did not induce the proliferation of peripheral blood T lymphocytes. Interestingly, when soluble anti-SC5 mAb was present together with immobilized anti-CD3 mAb, a significant inhibition of lymphocyte proliferation was observed. The inhibition varied between 33 and 66% at day 4 depending on the donor as compared to the effect of an isotype-matched irrelevant control mAb (see FIG. 5A, upper panel). As SC5 molecule is expressed on monocytes, it was important to determine whether the inhibitory effect was monocyte-independent. We studied the proliferation of two T cell clones, GDS.3 and LSO, stimulated by immobilized anti-CD3 mAb in the presence of anti-SC5 mAb or an isotype control mAb. The results obtained with both T cell clones indicated that engagement of SC5 molecules resulted in an inhibition of the proliferation to anti-CD3 mAb (see FIG. 5A, lower panel). It should be noted that the inhibitory effect of anti-SC5 mAb on T cell proliferation depended on its concentration, as well as on the concentration of the agonistic anti-CD3 mAb. The inhibition obtained with anti-SC5 mAb was significant only when T cells were stimulated with optimally diluted anti-CD3 mAb (see FIG. 5B). Such inhibitory behaviour was also reported for anti-KIRs mAbs (Cambiaggi et al. 1999, Blood 94: 2396-2402).

The decrease of T cell proliferation following SC5 engagement could be due to a direct induction of cell death, a perturbation of the IL-2R expression, or the inhibition of cytokine synthesis. We found that anti-SC5 mAb did not inhibit the IL-2-dependent proliferation of PBL or T cell clones (FIG. 5A). Furthermore, the addition of rIL-2 to T cells pre-incubated with anti-SC5 mAb (ascites diluted to 1/200) in combination with anti-CD3 for 48 h restored their proliferation. This would not be the case if the specific mAb inhibited IL-2R expression or caused cell death. Finally, in order to prove that SC5 triggering may inhibit cytokine production, we compared the amount of IL-2 secreted by anti CD3– activated PBL in the presence or absence of anti-SC5 mAb, using an IL-2 dependant T cell line. The quantity of IL-2 produced in the presence of anti-SC5 mAb represented 40 to 65% of the control values obtained with an isotype-matched antibody (see FIG. 5C). Thus, the simultaneous engagement of SC5 and CD3 molecules in T cells results in the decrease of cytokine production.

We next studied the effect of anti-SC5 mAb on T cell effector cytotoxic activity using an anti-CD3 mAb redirected killing assay against the FcgR+ murine cell line P815. FIG. 5D shows a representative experiment performed with a cytotoxic T cell clone at an E/T ratio of 5/1. The CD8+ T cell clone JF1, expressing high amount of SC5 molecules, was induced to kill murine target cells following anti-CD3 mAb stimulation. The simultaneous targeting of SC5 by its specific mAb did not influence JF1 cytotoxic activity, regardless of the F/T ratio or the concentration of stimulating anti-CD3 mAb.

Expression of SC5 Molecules on Malignant Lymphocytes Obtained from Patients with Sézary Syndrome As we initially screened anti-SC5 mAb for its reactivity with a CTCL cell line, we further studied the expression of SC5 molecule in the peripheral blood lymphocytes isolated from 8 patients with Sézary syndrome. Two-color flow cytometry analysis showed that expression of SC5 was significantly increased in the CD4+ subset (see representative results obtained with one patient in FIG. 6A). On the average, 35.5% of the CD4+ lymphocytes in SS patient blood expressed SC5 as compared to 9.4% in healthy controls ($p<0.001$), (FIG. 6B). In the 8 SS patients studied, the expression of SC5 on CD4+ cells correlated with the percentage of circulating malignant cells detected by cytomorphology ($r=0.91$, $p=0.0012$). It should be noted that in these patients the percentage of total CD4+ cells (mean=88%, SD±8.8) was higher than that of Sézary cells (mean=26%, SD±12.8).

We also studied SC5 molecule expression in peripheral blood samples from 3 MF patients without blood involvement. No significant difference in the levels of SC5 expression on peripheral blood CD4+ cells was observed between MF patients and healthy donors (FIG. 6B). Still, an increased percentage of SC5+CD4+ was detected in the skin samples from two of these patients, that we were able to test (26% and 19% respectively).

In one SS patient we had previously demonstrated that the circulating malignant cells were clonal lymphocytes with a CD4+TCRVβ22+ phenotype (Poszcepczynska et al. 2000, see supra). Here we demonstrated that SC5 was co-expressed on the TCRVβ22+ cells, i.e.—by the malignant cell population (FIG. 7A). It should be noted that the profile of SC5-mAb binding to TCRVβ22+ cells corresponded to a weak homogeneous expression on the whole malignant clonal cell population (FIG. 7B). Interestingly, the malignant TCRVβ22+ cells did not co-express common activation markers as CD69 (FIG. 7C), CD25 or CD30 as previously described (Poszcepczynska et al. 2000, see supra). Thus, the increased levels of SC5 in SS PBL were mostly due to the expression of the antigen on circulating malignant T cells.

Inhibition of the Anti-CD3mAb-Induced CTCL Cell Line Proliferation by Anti-SC5 mAb We next investigated whether SC5 molecules were able to provide a negative signal in malignant CTCL cells. We used the long-term cultured Pno CTCL tumor T cell line which strongly proliferates in the presence of IL-7. As previously reported that Pno cell line expresses functional T cell receptors, since immobilized anti-CD3 mAbs or the combination of soluble anti-CD3 mAbs and PMA induced significantly their proliferation (Poszcepczynska et al. 2000, see supra). We examined the effect of SC5 molecule engagement on the proliferation of Pno cells. FIG. 8 shows that anti-SC5 mAb strongly inhibited the anti-CD3 mAb-induced proliferation of the CTCL cell line. In contrast, PMA alone (2 ng/mL) produced a low level of proliferation which was not significantly affected by anti-SC5. Notably, anti-SC5 mAb had no effect on the IL-7-dependent proliferation, since Pno cells incubated with IL-7 in the presence of anti-SC5 mAb proliferated as vigorously as in the presence of the isotype control mAb. Thus, we concluded that SC5 antigen is functional in CTCL malignant cells and may specifically and profoundly inhibit their proliferation triggered through the TCR/CD3 signaling pathway.

A CTCL tumor was then successfully grafted onto transgenic mice having a substantial deficiency in functionally active NK cells and T lymphocytes (SCID mice) as described in Charley et al. (1990) "Establishment of a human cutaneous T cell lymphoma in CB-17 SCID mice" J. Invest. Dermatol. 94: 381-384 (see also U.S. Pat. No. 5,530,179 Cornelius P. Terhorst and Baoping Wang for obtention of SCID mice). Anti-SC5 mAb was intraveneously or intracutaneously administered at different times to half of the mice at various concentrations of purified mAb per gram of mouse, whereas the other half received the same amount of purified CD56 (isotype IgM) as a control. PBL and cutaneous cells were collected for standard cytological observations of infiltrating large T cells, and the percentage of CTCL cells was assessed for each mouse of the experiment. This procedure is an example of procedure that enables the skilled person to check that anti-SC5 compounds, such as the mAb produced by the hybridoma deposited as deposit number I-2575 at the C.N.C.M., are capable of inhibiting the in vivo proliferation of human CTCL.

Discussion

A number of receptors with dynamic surface expression mediate T cell interactions with other immune cells or cytokines and, consequently modulate T cell immune responses. In this study, we identified a novel 96 kD functional molecule expressed by a minor subset of PBL whose surface expression is induced rapidly during in vitro T-cell activation. SC5 is distinct from the established molecules with similar molecular weight and/or T cell modulatory functions. First, SC5 was induced very early upon T cell activation, with important increase of its surface expression detected after 4 h. A similar kinetics has been observed for the very early activation antigen CD69, which is detected on the cell surface between 2 and 4 h after stimulation. Most established T-cell specific inducible receptors such as 4-1BB, OX-40 LIGHT or CD152 (CTLA-4) appear on T-cell surface between 10 to 24 h following stimulation. Further, SC5 expression is not T cell restricted. The antigen was detected on sub-populations of NK and B lymphocytes, monocytes and granulocytes. Such a wide distribution pattern is typical of certain killer cell Ig-like receptors (KIRs), as the recently described AIRM1 and IRp60, which are found on NK cells, T and B lymphocytes, myeloid and other antigen-presenting cells. The family of immunoglobulin-like transcript (ILT) inhibitory receptors has also a pan-leukocyte type of expression, the individual receptors being detected on different NK, T, B and myeloid sub-populations. Moreover, ILT4 has a molecular weight very close to SC5. However, neither the expression of AIRM1 and IRp60, nor of ILTRs depends on the activation status of cells.

The prompt induction of SC5 molecule at the surface of activated T cells followed by its down-regulation may result from trafficking of intracellular molecules to the cell membrane and vice versa, as we detected SC5 in most non-activated T lymphocytes after cell permeabilization. Such a regulatory mechanism has been already reported for another T cell receptor, CD152. Further on, a heterogeneous family of lysosome associated membrane proteins (LAMP) exists, including molecules involved in endocytosis, lysosomal trafficking and secretion from intracellular granules and that may be induced on the surface of monocytes, neutrophiles, NK, B or T cells upon activation. Additional studies on the intracellular localization and transport of SC5 would precise its proper role in T cell activation and functions.

Our studies revealed that triggering of SC5 by its specific mAb inhibited the anti-CD3 mAb-induced T cell proliferation. This inhibitory effect required an optimal anti-CD3 mAb stimulation, which is necessary to induce maximal SC5 surface expression in PML (see FIG. 5B). A 1:200 final dilution of anti-SC5 ascites significantly inhibits the proliferation induced by anti-CD3 mAb at 2 microgram per well and this effect of inhibition increases with lower anti-CD3 mAb concentrations—1 microgram per well; 0.5 microgram per well. A 1:7100 final dilution of anti-SC5 ascites does not significantly inhibit the proliferation induced by anti-CD3 mAb at 2 microgram per well, but inhibition is significant when a lower concentration of anti-CD3 is used—1 microgram per well; 0.5 microgram per well. The person of ordinary skill in the art can proceed with such adjustments by standard interpolation from the particular results described herein, or from his own trials.

At the same time, the inhibitory threshold posed by SC5 engagement could be bypassed by excessive anti-CD3 mAb stimulation. It should be noted that the inhibitory functional effects obtained by ligation of SC5 molecules were observed in an APC-independent system. Further experiments are needed to determine whether SC5 stimulation may have different effects on the proliferation of APC- or allo-stimulated T cells. Recently, the negative regulation of immune responses has been extensively investigated, in particular in T lymphocytes and NK cells. The best studied T cell specific inhibitory receptor, CD152 (CTLA-4), is a typical activation-induced antigen, functionally coupled to CD28 co-stimulatory receptor. Indeed, CD152 may overcome CD28 positive signals at low antigenic concentrations and prevent immune response. Alternatively, it may downregulate and terminate T-cell proliferation induced through CD28 by affecting IL-2R expression and IL-2 synthesis. Similarly to CD152, SC5 is an intracellular molecule whose surface expression is regulated by the activation status of cells. Both receptors mediate their effects by affecting IL-2 synthesis. The identification of SC5 specific ligands and signaling pathways will precise the temporal and spatial correlation between these negative T-cell regulators.

In consideration to its wide cell distribution, SC5 functional effects are probably not restricted to T cells. In several aspects, SC5 is comparable to NK cell inhibitory receptors, equally expressed by T cells and other lymphocytes sub-populations. Both KIRs and CD94/NKG2 receptors were shown to inhibit antigen-specific and superantigen-driven activation of TCRαβ and TCRγδ T cells, including cytotoxicity, proliferation and cytokine secretion. The KIR-induced inhibition depends on the activation status of T cells and the potency of T cell stimulation and may be bypassed under specific in vivo conditions. However, SC5 is definitely distinct from KIRs, since we demonstrated that it selectively inhibited the proliferation of anti-CD3 mAb stimulated T cells without affecting their effector cytotoxic functions.

An important characteristic of SC5 molecule is its significantly increased expression in peripheral blood lymphocytes of patients with SS in comparison to healthy subjects. SS is characterized by the generalization of a primary epidermotropic malignant T cell clone with mature phenotype. Actually, none of the established T cell functional receptors conclusively identifies peripheral blood SS tumor cells. MF/SS has been considered as the expansion of a T cell subset with a particular phenotype, CD4+CD7−, corresponding to a normally existing T memory subset. However, a recent study demonstrated that the CD4+CD7− population does not always represent the dominant T cell clone in SS patients (Dummer et al. 1999, Arch. Dermatol. Res. 291: 307-311). SS is regarded as a proliferation of specifically activated T cells although the nature of the stimulus is not known (Fargnoli et al. 1997, Leukemia 11: 1338-1346). For this reason the distinct expression of activation induced antigens on SS and normal T cells is of special interest. Established activation antigens such as CD69, CD25, CD30 are not consistently detected on Sézary cells, as confirmed by our own investigations. Expression of CD25 rather correlates with the progression of the disease and the transformation of MF/SS cells into a large cell variant in a minority of the cases. An increased rate of expression of T cell activation molecules as HLA-DR, CD25 or CD71 in SS has been primarily associated with reactive tumor-infiltrating T cells. A 78 kD very late activation antigen, BE2, was reported to be specifically increased in SS peripheral blood, while not detected on normal T cells. In fact, BE2 was not consistently detected in all SS patients studied, a comparatively low percentage of peripheral blood cells in relation to the reported percentage of malignant cells were BE2-positive, and BE2 was equally detected in patients without clinical evidence of blood involvement. In contrast, SC5 was detected in 8/8 SS cases studied. Although the percentage of malignant cells determined by cytomorphology varied considerably from patient to patient (10-80%), the expression of SC5 on CD4+ cells correlated with this percentage. Finally, no elevated expression of SC5 on CD4+ cells was detected in MF patients without blood involvement. Further, we demonstrated that Sézary cells identified by the expression of the clonotypic TCRVβ chain co-expressed SC5 molecule, confirming that increased levels of SC5 in the peripheral blood of SS patients were due to its expression on the malignant T cell clone.

A very important observation was that SC5 triggering on Sézary cells induced down-modulation of the CD3-mediated proliferation of tumor cells, analogous to the inhibition observed in normal T cells. It has been already demonstrated that malignant CTCL lymphocytes preserve certain functional properties as they may be activated through basic signaling pathways although producing aberrant profiles of cytokines. We now demonstrate that an inhibitory pathway is preserved in CTCL tumor cells, that may permit to counterbalance their proliferation. Notably, the inhibitory effect observed after anti-SC5 mAb binding on anti-CD3 mAb-stimulated CTCL Pno cells was much more important than in normal T cells. Anti-SC5 mAb does not seem to directly mediate cell death of neither normal nor Sézary T cells, since it does not modulate the rIL-induced proliferation. Moreover, T-cells that had been cultivated in the presence of anti-SC5 mAb can be re-stimulated by addition of rIL-2. At the same time, we observed a diminished IL-2 production by anti-SC5 mAb-treated T cells, which should account at least partially for the inhibition of their proliferation.

Inhibitory effects of functional receptors on the proliferation of malignant cells have been already observed. It has been recently reported the inhibition of the proliferation of normal and leukemic myeloid cells mediated by the homologous NK cell sialoadhesin receptor AIRMI and CD33 myeloid-specific antigen (Vitale et al. 1999, Proc. Natl. Acad. Sci. USA 96: 15091-15096). Unlike SC5, these receptors inhibited proliferation in the presence of growth factors and most probably by induction of apoptosis. Interestingly, another T cell activation antigen, CD30, expressed by a subset of normal CD45RO+ T cells, is likely to mediate the regression of primary CTCL other than MF/SS. This effect is related to the natural ligand of CD30 (CD30L) which is co-located within the cytoplasm of malignant cells and may induce cytolytic cell death independently of Fas/FasL system (Mori et al. 1999, Blood 94: 3077-3083). In this aspect, the identification of SC5 ligand will enlighten the mechanism of its inhibitory action.

In conclusion, we have identified an early activation antigen which is distinct, by phenotypic, biochemical and functional criteria, from the established T lymphocyte receptors. As it was underlined, SC5 molecule is expressed by a subpopulation of the post-activation/memory peripheral blood T cell subset. Likewise, continuous expression of KIRs is detected on minor T cell clones, and this expression seems to depend on TCR-occupancy by specific antigens. It was recently proposed that such clones might be auto-reactive and maintained tolerant by KIRs signaling. We may speculate that SC5 surface expression is also preserved on auto-reactive T cells, suggesting that Sézary syndrome tumor cells possibly originate from such clones. Importantly, the expression of SC5 on CTCL malignant cells will serve to better define their origin and the nature of the signal driving mature T cells to uncontrolled proliferation. In addition, the inhibitory effect of anti-SC5 mAb on tumor T cells constitutes a novel therapeutic approach in patients with advanced CTCL.

Furthermore, expression of SC5 has also been observed at the surface of CD8+ CTCL, such as CD8+ transformed MF.

EXAMPLE 2 p140 is Expressed by CD4+ CTCL Cells, and Identification of a Novel p140 Allelic Form Cutaneous T-cell lymphomas (CTCL) are a heterogeneous group of lymphomas primarily involving the skin. Mycosis fungoides (MF) is characterized by skin invasion of clonally-derived malignant CD4+ T lymphocytes that phenotypically resemble mature T helper cells. A more aggressive form of CTCL develops when the malignant cells become non-epidermotropic and is associated with extra-cutaneous involvement. Sézary syndrome (SS) is a more aggressive form of CTCL that is characterized by a clonal expansion of CD4+/CD45RO+ T cells and the appearance of these malignant T cells in the blood. The biology of the disease remains poorly understood, as it is difficult to identify the malignant cell, due to the lack of specific cell surface markers. Thus, in cutaneous lesions it is difficult to distinguish CD4+ CTCL cells from reactive infiltrating CD4+ T lymphocytes. Bagot et al. previously described a unique CD4+ T cell line derived from CTCL lesions (Bagot et al. 1998, Blood 91: 4331-4341); this cell line and the in vivo tumor cells expressed an identical size of the complementarily-determining region 3 of TCR-Vβ transcripts. More recently, Poszepczynska et al. (Blood 2000, 96: 1056-1063) functionally characterized an IL-7-dependent CD4+CD8αα+ tumor T cell line isolated from the blood of another patient with a cutaneous erythrodermic CTCL.

This tumor T-cell line was identical to the major circulating T cell populations, as demonstrated by the expression of TCR-Vβ22 and the identity of the TCRβ3-VDJ sequences.

Here, we show that these two different CTCL lines express the p140/KIR inhibitory receptor for HLA-A alleles. Importantly, this receptor is detected on freshly isolated tumor cells derived from the same patients. Moreover, the p140/KIR was also co-expressed by a major subset of CD4+ lymphocytes in seven other patients with SS, and by tumor skin CD4+ cells in two additional patients with advanced MF. The p140/KIR is detected in normal individuals on a minor NK cell-subset and on rare peripheral blood CD3+CD8+ cells. Moreover, T cells obtained from skin in other dermatological diseases such as inflammatory skin diseases and toxic epidermal necrolysis did not express this receptor (Le Cleach et al. 2000, Clin. Exp. Immunol. 119: 225-230). Thus, our present findings demonstrate that the p140/KIR represents a suitable marker on CD4+ cells for the identification of CTCL.

Materials and Methods

Patients

After informed consent and approval by an ethic committee, we obtained skin and blood samples from eleven patients with a CTCL. Eight patients had a Sézary syndrome with 10 to 45% circulating Sézary cells in the blood. In seven cases, the phenotype of tumor cells was CD3+, CD4+, CD8–. In one case, the phenotype was CD3+, CD4+, CD8αα+ (patient Pno). Three patients had a transformed mycosis fungoides (Lez, Cou, Bic) and presented with disseminated skin tumors with a CD3+, CD4+, CD8– phenotype. All patients were not previously treated with chemotherapy.

Isolation of Tumoral Lymphocytes

Fresh CTCL tumor cells were obtained from tumor fragments mechanically dispersed into single-cell suspensions (Bagot et al. 1998, Blood 91: 4331-4341). The mononuclear cells were then washed and frozen in human serum plus 10% dimethyl sulfoxide for later use. For Sézary syndrome patients, the mononuclear blood cells were isolated by the technique of Ficoll-Isopaque (Pharmacia fine Chemicals, Piscataway, N.J.).

Long Term Culture of Tumor Cell Lines

We established the long term culture of Pno cell line (TCRVβ22+, CD3+, CD4+, CD8αα+, MHC class I+, MHC class II–) in vitro from the peripheral blood of the patient as previously described (Bagot et al. 1998, Blood 91: 4331-4341). We demonstrated that both the malignant clone circulating in the patient blood and the derived cultured T-cell line were identical for their cell surface phenotype and for their size and sequence of the TCRβ VDJ region (Poszepczynska et al. 2000, cf. supra). Other sources of SS cell lines may be found at the ATCC (e.g. HUT 78 ATCC TIB-161).

The Cou-L cell line (TCRVβ13+) was cultured in vitro with rIL-2 for more than three years. It corresponds to a subclone of the CD4+ Cou-LS CTCL line previously described (Bagot et al. 1998, cf supra). The Cou-L cell line, the original TCRVβ13+, CD4+ Cou-LS CTCL, and the tumor cells freshly isolated from the skin shared the same size and sequence of the TCRβ VDJ region (Bagot et al. 1998, cf. supra).

Monoclonal Antibodies (mAbs) and Flow Cytometry Studies

One- and two-color immunofluorescence analysis was performed as previously described (Bagot et al. 1998, cf. supra). Anti-CD3 (Cell Analysis 2000 catalogue reference 6604629), anti-CD4 (Cell Analysis 2000 catalogue reference 6602138), anti-MHC Class I (Cell Analysis 2000 catalogue reference IM0107) and II (Cell Analysis 2000 catalogue reference IM0108) are obtainable from Beckman Coulter (see Cell Analysis 2000 catalogue).

The anti-TCRVβ13+ mAb was purchased from Bioadvance (Emerainville, France, catalogue reference TCR 1738), and the anti-TCRVβ22+ mAb was obtained from Beckman-Coulter (Marseille, France, Cell Analysis 2000 catalogue reference IM 1484/IM1365). The anti-CD8 αβ 2ST8.5H7 mAb is obtainable from Beckman Coulter (Cell Analysis 2000 catalogue reference IM 2014. As anti-p140 mAbs, Q66 (IgM, anti-p140) and AZ158 (IgG2a, recognizing both p70/NKB1 and p140) which have been described in Pende et al. 1996 (J. Exp. Med. 184: 505-518) have been used; however any anti-140 binding compound is appropriate (e.g. anti-p140 antiserum, Fc-HLA-A11, Fc-HLA-A3 fusion proteins). Z27 (IgG1, anti-p70/NKB1), EB6 (IgG1, anti-p58.1/p50.1), GL183 (IgG1, anti-p58.2/p50.2), XA185 (IgG1, anti-CD94), 2199 and Z270 (IgG2b and IgG2a respectively, anti-NKG2A), and B9.4 (IgG2b, anti-CD8) mAbs are all obtainable from Beckman Coulter (see Cell Analysis 2000 catalogue references IM2748, IM2277, IM2278, IM1610, IM2750, IM0102).

Goat anti-mouse IgG FITC and goat anti-mouse IgM PE are also obtainable from Beckman Coulter (see Cell Analysis Catalogue references IM08 and IM0555).

Biochemical Characterization $20 \times 10^6$ cells were incubated (15' at 20° C.) in 1 ml PBS pH8 containing 250 µg of EZ-LINK SULFO-NHS-LC-LC-BIOTIN (Pierce, Rockford, Ill.) and washed three times in Washing Buffer (10 mM TRIS pH 8, 0.14 M NaCl). Cells were then lysed in 1% NP-40 and immuno-precipitated with Sepharose-PA (Pharmacia Biotech Inc. Piscataway, N.J.)—coupled AZ158 (IgG2a, antip70/140) or B9.4 (IgG2b, anti-CD8) mAbs. Samples were analyzed by discontinuous SDS-PAGE either undigested or digested with N-glycosidase F (Boehringer Mannheim, GmbH, Germany) and transferred to Immobilon P (Millipore Corp, Bedform, Mass.). After staining with Neutravidin (Pierce) the Renaissance Chemiluminescence Kit (NEN, Boston, Mass.) was used for detection. NK cell clones were obtained by limiting dilution as described in Pende et al. 1996 (J. Exp. Med. 184: 505-518).

RT-PCR Analysis

Total RNA was extracted from CTCL cell lines Pno and Cou-LCD8 αα using RNA-Clean System (AGS GmbH, Heidelberg, Germany). cDNA synthesis was performed using oligodT priming. Primers used for cDNA amplification of the complete ORF (open reading frame) of KIR displaying three Ig-like domains (1395 bp) were the following: 5'CATGT(CT)GCTCA(CT)GGTCGTC (Ig3 UP; SEQ ID No. 5) and 5' GGTTTTGAGACAGGGCTG (Ig3 DOWN; SEQ ID No. 6). Amplification was performed for 30 cycles (30 sec. at 94° C., 30 sec. at 55° C., 30 sec. at 72° C.), followed by a 7 min. incubation at 72° C., utilizing AmpliTAQ (Perkin Elmer-Applied Biosystems, Foster City, Calif.). PCR products were sub-cloned into pcDNA3.1/V5-His-TOPO vector (Invitrogen, Carlsbad, Calif.). DNA sequencing was performed using d-Rhodamine Terminator Cycle Sequencing Kit and a 377 Applied Biosystems Automatic Sequencer (Perkin Elmer-Applied Biosystems).

Transient Transfections

COS-7 cells were transfected with pcDNA3.1 TOPO-KIR3D cl.24 or with pCR3-cl.1.1 (Pende et al. 1996, J. Exp. Med. 184: 505-518) utilizing Fugene 6 (Roche, Monza Italy). Briefly, cells were seeded at $5 \times 10^5$/plate; 24 hr later they were incubated with 6 µg plasmid and 10 µl of Fugene-6 reagent in DMEM/10% FCS. After 48 or 72 his, transfected cells were used for cytofluorimetric analysis. Cell transfectants were stained with Q66 and AZ158 mAbs, followed by a phycoerythrin-conjugated goat antibody to mouse IgG2a or IgM and analyzed by flow cytometry using a FACSort (Becton Dickinson, San Jose, Calif.).

Results

CTCL Cell Lines are Stained by mAbs to the p140/KIR

Two long-term CTCL tumor lines Pno (labeled with anti-TCR-Vβ22 mAb) (Poszepczynska et al. 2000, cf supra) and Cou-L (labeled with anti-CD3 mAb) (Bagot et al. 1998, cf. supra) were analyzed for reactivity with different anti-KIR mAbs. We found that both cell lines were reactive with mAbs Q66 (see FIG. 9A) and AZ158, both recognizing the p140/KIR. In contrast, these cell lines did not express other inhibitory receptors specific for HLA class I molecules, including p58.1, p58.2, p70 KIRs and the CD94/NKG2A lectin-like receptor (Poszepczynska et al. 2000, cf supra).

Tumor T Lymphocytes Freshly Isolated from CTCL Patients are Stained by Anti-p140/KIR mAbs To determine whether p140/KIR was expressed by freshly isolated tumor cells, we tested the reactivity of Q66 mAb with uncultured tumor cells isolated from the blood in SS patient Pno and from tumoral skin fragments of MF patient Cou. We found that the majority of tumor cells were stained by this mAb (FIG. 9B). In particular, we observed that most TCRVβ22+ tumor lymphocytes isolated from the blood of patient Pno were reactive with Q66 antibody, and that most of the TCRVβ13+ tumor lymphocytes isolated from the skin of patient Cou were stained by the same antibody (FIG. 9B).

Next, we studied the phenotype of tumor T lymphocytes from the blood of seven additional patients with a Sézary syndrome, with malignant cells representing 10 to 45% of circulating CD4+ lymphocytes, and tumor T lymphocytes isolated from skin tumors of two other patients with a MF. Remarkably, all patients tested exhibited a significant population co-expressing CD4 and p140/KIR (see Table 2 below).

TABLE 2

Anti-Q66 mAb stained CD4+ lymphocytes isolated from the skin of patients with transformed mycosis fungoides and from blood of patients with Sézary syndrome.

| | Percentage of positive cells with | |
|---|---|---|
| Patient samples | anti-CD4 mAb | anti-CD4 mAb + anti-Q66 mAb |
| MF | | |
| Lez | 65 | 29 |
| Bic | 53 | 44 |
| SS | | |
| Bri | 85 | 35 |
| Bar | 90 | 18 |
| Att | 95 | 35 |
| Ros | 98 | 15 |
| Can | 78 | 36 |
| Pet | 45 | 9 |
| Riv | 98 | 19 |

It should be noted that all Q66+ cells were included in the CD4+ cell population. Thus, the expression of p140/KIR, which in normal individuals is restricted to subsets of lymphocytes from the NK and CD8+ populations, appears to be a characteristic of CTCL tumor CD4+ T lymphocytes, both in the skin and in the blood. As control, skin T lymphocytes derived from another dermatological disease, toxic epidermal necrolysis, which were shown to contain small percentages of various KIR expressing T lymphocytes (Le Cleach et al. 2000, Clin. Exp. Immunol. 119: 225-230), failed to express p140/KIR.

Molecular Characterization of the p140 Receptor Expressed by CTCL.

The Pno and Cou-L cell lines were surface labeled with biotin and cell lysates were immuno-precipitated with an anti-p140 (AZ158 mAb). As shown in FIG. 10, this mAb immuno-precipitated from a NK clone and from the Pno and Cou-L cell lines a molecule with a molecular mass of approximately 70 kD under reducing conditions. Treatment with N-glycosidase revealed a protein backbone of approximately 50 kD with a slightly higher mobility for Pno and Cou-L compared to NK clone. These data suggested that the p140 inhibitory receptor expressed by these CTCL tumor cell lines could be almost similar to that previously detected on normal NK cells (Pende et al. 1996, J. Exp. Med. 184: 505-518).

Next, we determined whether the cDNA encoding the molecule recognized by Q66 and AZ158 mAbs on Pno and Cou-L CTCL cell lines corresponded to one of the already described cDNA encoding p140/KIR (SEQ ID No. 3). To this end, RT-PCR was performed on RNA derived from these cell lines using a set of primers able to amplify all cDNA encoding KIR with three Ig-like domains. From the Pno cell line, we isolated a full-length cDNA, termed KIR3D cl.24 (SEQ ID No. 1). Comparison of its nucleotide sequence with DNA sequences coding for all KIR characterized by three extra-cellular Ig-like domains revealed that KIR3D cl.24 represents a novel allelic form of p140 receptor. In particular, its nucleotide sequence displays five differences compared to the previously described cl. 1.1 cDNA (Pende et al. 1996, J. Exp. Med. 184: 505-518), resulting in four amino acid substitutions in the mature protein (see FIG. 11; SEQ ID No. 2: clone 24 protein; SEQ ID No. 4: clone 1.1 protein). Three of the four substitutions are found in the extra-cellular Ig-like domain (pos. 20, 92 and 111 of the mature protein), whereas the other is located in the cytoplasmic region (pos.401). RT-PCR performed on Cou-L CTCL cell line revealed two different allelic forms of p140/KIR one corresponding to cl. 1.1 cDNA and the other identical to KIR3D cl.24 (isolated from Pno cell line). The cDNA derived from the CTCL cell lines were then transiently transfected in COS-7 cells. As expected, all cell transfectants were brightly stained by Q66 and AZ158 mAb, while they were unreactive with p70/KIR-specific Z27 mAb used as a negative control. Finally, RT-PCR was performed on RNA extracted from PBL derived from three SS patients (including patient Pno) and from skin-derived T cells of one additional MF patients. Also in these samples one or another allelic isoform of p140/KIR described above could be identified.

The same results were obtained on malignant CTCL cells collected from patients.

Discussion

Skin lesions in CTCL contain a heterogeneous lymphocytic infiltrate composed of malignant T cells, which are most often. CD4+, and non-neoplastic tumor infiltrating T lymphocytes. We previously reported CD4+ cytotoxic tumor infiltrating lymphocytes specifically directed against autologous malignant CTCL CD4+ cell line. However, as no tumor restricted cell surface structure, besides the clonotypic TCR expressed by tumor cells, has been identified on CTCL, it is difficult using standard methods to distinguish malignant from non-malignant reactive CD4+ lymphocytes.

In the present study, we report for the first time that tumor cells from MF and SS patients express the p140/KIR. This receptor has been identified in both skin and blood tumor cells from CTCL patients as well as in two long-term culture CTCL lines. Two color fluorescence analysis indicated that p140/KIR expression is restricted to T cells characterized by a given TCRβ-VDJ previously identified on tumor cells.

Thus, p140/KIR allows rapid identification of tumor cells from tumor reactive cells among the T lymphocyte CD4+ population. This could be particularly useful in SS patients, in which the tumor T cell clone is not always easily identified within the peripheral blood CD4+ lymphocyte population. Moreover, during the course of the disease or after treatment, it is crucial to assess whether an increase of the CD4+ population is due to an expansion of the tumor cell population or of reactive T lymphocytes, Since the anti-p140/KIR mAbs appear to recognize tumor cells in all CTCL patients analyzed, they may be considered as a suitable tool for the direct identification of CTCLs. In addition, the use of p140/KIR co-expression on CD4+ CTCL cells provides a unique tool to distinguish malignant cells from normal cells in every patient. This is in contrast to TCR determinations which is unique to an individual patient. Moreover, the p140/KIR represents a possible target for the development of novel specific immunotherapy of CTCL.

Previous studies indicated that this receptor was able to generate inhibitory signals upon recognition of HLA.A3 and HLA.A11 alleles. It is of note, however, that p140/KIR expression in the various patients analyzed appears apparently independent from their own HLA Class I haplotype. Nevertheless, the actual role of p140/KIR in the patho-physiology of CTCL is an important feature that remains to be studied by taking into account the potential role of this receptor in the tolerance to self In conclusion, the present study demonstrates for the first time the expression of the p140/KIR in CD4+CTCL cells and the isolation of a novel allelic form of this receptor in tumor cells. This finding is an important new issue, both for the patho-physiology and for the clinical management of CTCL patients.

Furthermore, p140 expression has also been observed at the surface of CD8+ CL such as CD8+ transformed MF.

EXAMPLE 3

Production of Anti-CTCL Drugs

The person of ordinary skill in the art is enabled to produce anti-CTCL drugs pursuant to the following outlines, given for illustration purposes:
- use of anti-SC5 or anti-p140 mAb with a cytokine such as Interferon gamma or IL-2 for stimulating the immune system of cells in the vicinity of CTCL cells,
- use of these anti-SC5 and anti-p140 mAb as vectors for delivering anti-CTCL ingredients onto CTCL cells; examples of anti-CTCL ingredients comprise standard compounds used in chimiotherapy such as radioelements, toxines.

mAb vectors for radioelements can be produced following standard techniques applied to an anti-SC5 mAb of the invention (see e.g. Press O W et al. "Phase two trial of iode131-B1 (anti-CD20) antibody therapy with autologous stem cell transplantation for relapsed B cell lymphoma", Lancet 1995 vol. 346 pp 336-340, of which content is herein incorporated by reference).

mAb vectors for toxine can be produced following standard techniques applied to an anti-SC5 mAb of the invention (see e.g. Ghetie U et al. "Large scale preparation of an immunoconjuguate constructed with human recombinant CD4 and deglycosylated ricin A chain", J. Immunol. Methods 1990, vol. 126 pp 135-141, of which content is herein incorporated by reference).

- combined use of an antimitotic pro-drug and of anti-SC5 mAb and/or anti-p140 mAb vectors delivering an enzyme capable of transforming an antimitotic pro-drug to the active drug form (mitotic agent in a functional form).

Anti-SC5 mAb and anti-p140 mAb vectors delivering an enzyme capable of transforming an antimitotic pro-drug to the active drug form can be produced following standard techniques applied to an anti-SC5 mAb of the invention and to an anti-p140 mAb (see e.g. the ADEPT technique, for Antibody Directed Enzyme Prodrug Therapy, described in Plakey T C et al. "Anti-tumor effects of an antibody-carboxypeptidase G2 conjuguate in combination with phenol mustard prodrugs", British J. Cancer 1995 vol. 72 pp 1083-1088, of which content is herein incorporated by reference).

- use of anti-SC5 or anti-p140 mAb as ligand agonists (SC5 stimulation or p140 stimulation)
- use of anti-SC5 or anti-p140 mAb as complement recruiting agent For the above-mentioned uses, mAbs with a double anti-SC5/anti-CD4 or anti-p 140/anti-CD4 specificity are preferred.

- use of anti-SC5 or anti-p140 (no CD4+ specificity needed) as activators of ADCC (Antibody Dependent Cell Cytotoxicity): polynuclear cells, macrophages, NK cells bear Fc receptors which are activated by the Fc portion of the anti-SC5 and anti-p 140 mAb, these mAb therefore enable the ADCC activation in the vicinity of CTCL cells.

Abbreviations:

APC: Antigen Presenting Cell, CTCL: cutaneous T cell lymphoma, DIG: detergent-insoluble glycolipid-enriched fraction, ILT: immunoglobulin-like transcript, KIR: killer cell immunoglobulin receptor, mAb: monoclonal antibody, MF: mycosis fungoides, PBL: peripheral blood lymphocytes, PBMC: peripheral blood mononuclear cells, PHA: phytohemagglutinin, PMA: phorbol12 beta-myristate13 alpha-acetate, SS: Sézary syndrome, TCR: T cell receptor.

We claim:

1. A method for treating a T-cell malignancy comprising administering a pharmaceutical composition comprising an antibody that binds to a polypeptide comprising SEQ ID NO: 2 to a subject having a T-cell malignancy, said polypeptide being expressed on the surface of a malignant T-cell.

2. The method according to claim 1, wherein said antibody further comprises a molecule capable of inducing the death of said malignant T-cell.

3. The method according to claim 2, wherein said antibody further comprises a radioelement or a toxin.

4. The method according to claim 1, wherein said antibody stimulates antibody dependent cellular cytotoxicity (ADCC).

5. The method according to claim 1, wherein said antibody recruits complement to the surface of said malignant T-cell.

6. The method according to claim 1, wherein said T-cell malignancy is a cutaneous T cell lymphoma.

7. The method according to claim 1, wherein said antibody is a humanized antibody.

8. The method according to claim 2, wherein said body is a humanized antibody.

9. The method according to claim 3, wherein said antibody is a humanized antibody.

10. The method according to claim 4, wherein said antibody is a humanized antibody.

11. The method according to claim 5, wherein said antibody is a humanized antibody.

12. The method according to claim 1, wherein said T-cell malignancy is a T cell lymphoma.

* * * * *

UNITED STATES PATENT AND TRADEMARK OFFICE
CERTIFICATE OF CORRECTION

PATENT NO. : 8,268,308 B2  
APPLICATION NO. : 13/008406  
DATED : September 18, 2012  
INVENTOR(S) : Armand Bensussan et al.

Page 1 of 1

It is certified that error appears in the above-identified patent and that said Letters Patent is hereby corrected as shown below:

Column 5,  
Line 60, "or PM," should read --or PBL,--.

Column 10,  
Line 28, "Freeman air." should read --Freeman G. J.--.

Column 18,  
Line 3, "CD4-CTCL" should read --CD4 + CTCL--.

Column 24,  
Lines 12-13, "LSO (CD3+TCRγδ6+CD4-CD8-)" should read  
--LSO (CD3+TCRγδ+CD4-CD8-)--.

Column 28,  
Lines 21-22, "of the F/T ratio" should read --of the E/T ratio--.

Column 30,  
Line 20, "in PML" should read --in PBL--.  
Line 25, "A 1:7100 final" should read --A 1:400 final--.

Column 34,  
Line 17, "2199" should read --Z199--.

Column 50,  
Line 42, "said body" should read --said antibody--.

Signed and Sealed this  
Second Day of April, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,268,308 B2  Page 1 of 1
APPLICATION NO. : 13/008406
DATED : September 18, 2012
INVENTOR(S) : Armand Bensussan et al.

It is certified that error appears in the above-identified patent and that said Letters Patent is hereby corrected as shown below:

In the Specifications:
Column 5,
Line 60, "or PM," should read --or PBL,--.

Column 10,
Line 28, "Freeman air." should read --Freeman G. J.--.

Column 18,
Line 13, "CD4-CTCL" should read --CD4 + CTCL--.

Column 24,
Lines 12-13, "LSO (CD3+TCRγδ6+CD4-CD8-)" should read
--LSO (CD3+TCRγδ+CD4-CD8-)--.

Column 28,
Lines 21-22, "of the F/T ratio" should read --of the E/T ratio--.

Column 30,
Line 20, "in PML" should read --in PBL--.
Line 25, "A 1:7100 final" should read --A 1:400 final--.

Column 34,
Line 17, "2199" should read --Z199--.

In the Claims:
Column 50,
Line 42, "said body" should read --said antibody--.

This certificate supersedes the Certificate of Correction issued April 2, 2013.

Signed and Sealed this
Twenty-first Day of May, 2013

Teresa Stanek Rea
*Acting Director of the United States Patent and Trademark Office*

SEQUENCE LISTING

```
<160> NUMBER OF SEQ ID NOS: 6

<210> SEQ ID NO 1
<211> LENGTH: 1395
<212> TYPE: DNA
<213> ORGANISM: Homo sapiens
<220> FEATURE:
<221> NAME/KEY: CDS
<222> LOCATION: (65)...(1369)

<400> SEQUENCE: 1
catgtcgctc actgtcgtca gcatggcgtg cgttgggttc ttcttgctgc aggggggcctg      60
```

```
gcca ctc atg ggt ggt cag gac aaa ccc ttc ctg tct gcc cgg ccc agc    109
     Leu Met Gly Gly Gln Asp Lys Pro Phe Leu Ser Ala Arg Pro Ser
      1               5                  10                  15 act gtg gtg cct caa gga gga cac gtg gct ctt cag tgt cac tat cgt    157
Thr Val Val Pro Gln Gly Gly His Val Ala Leu Gln Cys His Tyr Arg
                 20                  25                  30 cgt ggg ttt aac aat ttc atg ctg tac aaa gaa gac aga agc cac gtt    205
Arg Gly Phe Asn Asn Phe Met Leu Tyr Lys Glu Asp Arg Ser His Val
             35                  40                  45 ccc atc ttc cac ggc aga ata ttc cag gag agc ttc atc atg ggc cct    253
Pro Ile Phe His Gly Arg Ile Phe Gln Glu Ser Phe Ile Met Gly Pro
         50                  55                  60 gtg acc cca gca cat gca ggg acc tac aga tgt cgg ggt tca cgc cca    301
Val Thr Pro Ala His Ala Gly Thr Tyr Arg Cys Arg Gly Ser Arg Pro
     65                  70                  75 cac tcc ctc act ggg tgg tcg gca ccc agc aac ccc ctg gtg atc atg    349
His Ser Leu Thr Gly Trp Ser Ala Pro Ser Asn Pro Leu Val Ile Met
 80                  85                  90                  95 gtc aca gga aac cac aga aaa cct tcc ctc ctg gcc cac cca ggg acc    397
Val Thr Gly Asn His Arg Lys Pro Ser Leu Leu Ala His Pro Gly Thr
                    100                 105                 110 ctg ctg aaa tca gga gag aca gtc atc ctg caa tgt tgg tca gat gtc    445
Leu Leu Lys Ser Gly Glu Thr Val Ile Leu Gln Cys Trp Ser Asp Val
                115                 120                 125 atg ttt gag cac ttc ttt ctg cac aga gag ggg atc tct gag gac ccc    493
Met Phe Glu His Phe Phe Leu His Arg Glu Gly Ile Ser Glu Asp Pro
            130                 135                 140 tca cgc ctc gtt gga cag atc cat gat ggg gtc tcc aag gcc aac ttc    541
Ser Arg Leu Val Gly Gln Ile His Asp Gly Val Ser Lys Ala Asn Phe
145                 150                 155 tcc atc ggt ccc ttg atg cct gtc ctt gca gga acc tac aga tgt tat    589
Ser Ile Gly Pro Leu Met Pro Val Leu Ala Gly Thr Tyr Arg Cys Tyr
160                 165                 170                 175 ggt tct gtt cct cac tcc ccc tat cag ttg tca gct ccc agt gac ccc    637
Gly Ser Val Pro His Ser Pro Tyr Gln Leu Ser Ala Pro Ser Asp Pro
                180                 185                 190 ctg gac atc gtg atc aca ggt cta tat gag aaa cct tct ctc tca gcc    685
Leu Asp Ile Val Ile Thr Gly Leu Tyr Glu Lys Pro Ser Leu Ser Ala
            195                 200                 205 cag ccg ggc ccc acg gtt cag gca gga gag aac gtg acc ttg tcc tgt    733
Gln Pro Gly Pro Thr Val Gln Ala Gly Glu Asn Val Thr Leu Ser Cys
        210                 215                 220 agc tcc tgg agc tcc tat gac atc tac cat ctg tcc agg gaa ggg gag    781
Ser Ser Trp Ser Ser Tyr Asp Ile Tyr His Leu Ser Arg Glu Gly Glu
225                 230                 235 gcc cat gaa cgt agg ctc cgt gca gtg ccc aag gtc aac aga aca ttc    829
Ala His Glu Arg Arg Leu Arg Ala Val Pro Lys Val Asn Arg Thr Phe
240                 245                 250                 255 cag gca gac ttt cct ctg ggc cct gcc acc cac gga ggg acc tac aga    877
Gln Ala Asp Phe Pro Leu Gly Pro Ala Thr His Gly Gly Thr Tyr Arg
                260                 265                 270 tgc ttc ggc tct ttc cgt gcc ctg ccc tgc gtg tgg tca aac tca agt    925
Cys Phe Gly Ser Phe Arg Ala Leu Pro Cys Val Trp Ser Asn Ser Ser
            275                 280                 285 gac cca ctg ctt gtt tct gtc aca gga aac cct tca agt agt tgg cct    973
Asp Pro Leu Leu Val Ser Val Thr Gly Asn Pro Ser Ser Ser Trp Pro
        290                 295                 300 tca ccc aca gaa cca agc tcc aaa tct ggt atc tgc aga cac ctg cat   1021
Ser Pro Thr Glu Pro Ser Ser Lys Ser Gly Ile Cys Arg His Leu His
305                 310                 315
```

```
gtt ctg att ggg acc tca gtg gtc atc ttc ctc ttc atc ctc ctc ctc     1069
Val Leu Ile Gly Thr Ser Val Val Ile Phe Leu Phe Ile Leu Leu Leu
320                 325                 330                 335 ttc ttt ctc ctt tat cgc tgg tgc tcc aac aaa aag aat gct gct gta     1117
Phe Phe Leu Leu Tyr Arg Trp Cys Ser Asn Lys Lys Asn Ala Ala Val
                340                 345                 350 atg gac caa gag cct gcg ggg gac aga aca gtg aat agg cag gac tct     1165
Met Asp Gln Glu Pro Ala Gly Asp Arg Thr Val Asn Arg Gln Asp Ser
            355                 360                 365 gat gaa caa gac cct cag gag gtg acg tac gca cag ttg gat cac tgc     1213
Asp Glu Gln Asp Pro Gln Glu Val Thr Tyr Ala Gln Leu Asp His Cys
        370                 375                 380 gtt ttc ata cag aga aaa atc agt cgc cct tct cag agg ccc aag aca     1261
Val Phe Ile Gln Arg Lys Ile Ser Arg Pro Ser Gln Arg Pro Lys Thr
385                 390                 395 ccc cca aca gat acc agc gtg tac acg gaa ctt cca aat gct gag ccc     1309
Pro Pro Thr Asp Thr Ser Val Tyr Thr Glu Leu Pro Asn Ala Glu Pro
400                 405                 410                 415 aga tcc aaa gtt gtc tcc tgc cca cga gca cca cag tca ggt ctt gag     1357
Arg Ser Lys Val Val Ser Cys Pro Arg Ala Pro Gln Ser Gly Leu Glu
                420                 425                 430 ggg gtt ttc tag ggagacaaca gccctgtctc aaaacc                        1395
Gly Val Phe *

<210> SEQ ID NO 2
<211> LENGTH: 434
<212> TYPE: PRT
<213> ORGANISM: Homo sapiens

<400> SEQUENCE: 2

Leu Met Gly Gly Gln Asp Lys Pro Phe Leu Ser Ala Arg Pro Ser Thr
1               5                   10                  15

Val Val Pro Gln Gly Gly His Val Ala Leu Gln Cys His Tyr Arg Arg
            20                  25                  30

Gly Phe Asn Asn Phe Met Leu Tyr Lys Glu Asp Arg Ser His Val Pro
        35                  40                  45

Ile Phe His Gly Arg Ile Phe Gln Glu Ser Phe Ile Met Gly Pro Val
    50                  55                  60

Thr Pro Ala His Ala Gly Thr Tyr Arg Cys Arg Gly Ser Arg Pro His
65                  70                  75                  80

Ser Leu Thr Gly Trp Ser Ala Pro Ser Asn Pro Leu Val Ile Met Val
                85                  90                  95

Thr Gly Asn His Arg Lys Pro Ser Leu Leu Ala His Pro Gly Thr Leu
            100                 105                 110

Leu Lys Ser Gly Glu Thr Val Ile Leu Gln Cys Trp Ser Asp Val Met
        115                 120                 125

Phe Glu His Phe Phe Leu His Arg Glu Gly Ile Ser Glu Asp Pro Ser
    130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
            180                 185                 190

Asp Ile Val Ile Thr Gly Leu Tyr Glu Lys Pro Ser Leu Ser Ala Gln
        195                 200                 205

Pro Gly Pro Thr Val Gln Ala Gly Glu Asn Val Thr Leu Ser Cys Ser
```

```
                210                 215                 220
Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
                260                 265                 270

Phe Gly Ser Phe Arg Ala Leu Pro Cys Val Trp Ser Asn Ser Ser Asp
                275                 280                 285

Pro Leu Leu Val Ser Val Thr Gly Asn Pro Ser Ser Ser Trp Pro Ser
290                 295                 300

Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
                325                 330                 335

Phe Leu Leu Tyr Arg Trp Cys Ser Asn Lys Lys Asn Ala Ala Val Met
                340                 345                 350

Asp Gln Glu Pro Ala Gly Asp Arg Thr Val Asn Arg Gln Asp Ser Asp
                355                 360                 365

Glu Gln Asp Pro Gln Glu Val Thr Tyr Ala Gln Leu Asp His Cys Val
370                 375                 380

Phe Ile Gln Arg Lys Ile Ser Arg Pro Ser Gln Arg Pro Lys Thr Pro
385                 390                 395                 400

Pro Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
                420                 425                 430

Val Phe

<210> SEQ ID NO 3
<211> LENGTH: 1395
<212> TYPE: DNA
<213> ORGANISM: Homo sapiens
<220> FEATURE:
<221> NAME/KEY: CDS
<222> LOCATION: (65)...(1369)

<400> SEQUENCE: 3
catgtcgctc acggtcgtca gcatggcgtg cgttgggttc ttcttgctgc aggggggcctg      60 gcca ctc atg ggt ggt cag gac aaa ccc ttc ctg tct gcc cgg ccc agc      109
     Leu Met Gly Gly Gln Asp Lys Pro Phe Leu Ser Ala Arg Pro Ser
      1               5                  10                  15 act gtg gtg cct cga gga gga cac gtg gct ctt cag tgt cac tat cgt      157
Thr Val Val Pro Arg Gly Gly His Val Ala Leu Gln Cys His Tyr Arg
              20                  25                  30 cgt ggg ttt aac aat ttc atg ctg tac aaa gaa gac aga agc cac gtt      205
Arg Gly Phe Asn Asn Phe Met Leu Tyr Lys Glu Asp Arg Ser His Val
          35                  40                  45 ccc atc ttc cac ggc aga ata ttc cag gag agc ttc atc atg ggc cct      253
Pro Ile Phe His Gly Arg Ile Phe Gln Glu Ser Phe Ile Met Gly Pro
      50                  55                  60 gtg acc cca gca cat gca ggg acc tac aga tgt cgg ggt tca cgc cca      301
Val Thr Pro Ala His Ala Gly Thr Tyr Arg Cys Arg Gly Ser Arg Pro
 65                  70                  75 cac tcc ctc act ggg tgg tcg gca ccc agc aac ccc gtg gtg atc atg      349
His Ser Leu Thr Gly Trp Ser Ala Pro Ser Asn Pro Val Val Ile Met
 80                  85                  90                  95
```

```
gtc aca gga aac cac aga aaa cct tcc ctc ctg gcc cac cca ggg ccc    397
Val Thr Gly Asn His Arg Lys Pro Ser Leu Leu Ala His Pro Gly Pro
            100             105             110 ctg ctg aaa tca gga gag aca gtc atc ctg caa tgt tgg tca gat gtc    445
Leu Leu Lys Ser Gly Glu Thr Val Ile Leu Gln Cys Trp Ser Asp Val
        115             120             125 atg ttt gag cac ttc ttt ctg cac aga gag ggg atc tct gag gac ccc    493
Met Phe Glu His Phe Phe Leu His Arg Glu Gly Ile Ser Glu Asp Pro
    130             135             140 tca cgc ctc gtt gga cag atc cat gat ggg gtc tcc aag gcc aac ttc    541
Ser Arg Leu Val Gly Gln Ile His Asp Gly Val Ser Lys Ala Asn Phe
145             150             155 tcc atc ggt ccc ttg atg cct gtc ctt gca gga acc tac aga tgt tat    589
Ser Ile Gly Pro Leu Met Pro Val Leu Ala Gly Thr Tyr Arg Cys Tyr
160             165             170             175 ggt tct gtt cct cac tcc ccc tat cag ttg tca gct ccc agt gac ccc    637
Gly Ser Val Pro His Ser Pro Tyr Gln Leu Ser Ala Pro Ser Asp Pro
            180             185             190 ctg gac atc gtg atc aca ggt cta tat gag aaa cct tct ctc tca gcc    685
Leu Asp Ile Val Ile Thr Gly Leu Tyr Glu Lys Pro Ser Leu Ser Ala
        195             200             205 cag ccg ggc ccc acg gtt cag gca gga gag aac gtg acc ttg tcc tgt    733
Gln Pro Gly Pro Thr Val Gln Ala Gly Glu Asn Val Thr Leu Ser Cys
    210             215             220 agc tcc tgg agc tcc tat gac atc tac cat ctg tcc agg gaa ggg gag    781
Ser Ser Trp Ser Ser Tyr Asp Ile Tyr His Leu Ser Arg Glu Gly Glu
225             230             235 gcc cat gaa cgt agg ctc cgt gca gtg ccc aag gtc aac aga aca ttc    829
Ala His Glu Arg Arg Leu Arg Ala Val Pro Lys Val Asn Arg Thr Phe
240             245             250             255 cag gca gac ttt cct ctg ggc cct gcc acc cac gga ggg acc tac aga    877
Gln Ala Asp Phe Pro Leu Gly Pro Ala Thr His Gly Gly Thr Tyr Arg
            260             265             270 tgc ttc ggc tct ttc cgt gcc ctg ccc tgc gtg tgg tca aac tca agt    925
Cys Phe Gly Ser Phe Arg Ala Leu Pro Cys Val Trp Ser Asn Ser Ser
        275             280             285 gac cca ctg ctt gtt tct gtc aca gga aac cct tca agt agt tgg cct    973
Asp Pro Leu Leu Val Ser Val Thr Gly Asn Pro Ser Ser Ser Trp Pro
    290             295             300 tca ccc aca gaa cca agc tcc aaa tct ggt atc tgc aga cac ctg cat    1021
Ser Pro Thr Glu Pro Ser Ser Lys Ser Gly Ile Cys Arg His Leu His
305             310             315 gtt ctg att ggg acc tca gtg gtc atc ttc ctc ttc atc ctc ctc ctc    1069
Val Leu Ile Gly Thr Ser Val Val Ile Phe Leu Phe Ile Leu Leu Leu
320             325             330             335 ttc ttt ctc ctt tat cgc tgg tgc tcc aac aaa aag aat gct gct gta    1117
Phe Phe Leu Leu Tyr Arg Trp Cys Ser Asn Lys Lys Asn Ala Ala Val
            340             345             350 atg gac caa gag cct gcg ggg gac aga aca gtg aat agg cag gac tct    1165
Met Asp Gln Glu Pro Ala Gly Asp Arg Thr Val Asn Arg Gln Asp Ser
        355             360             365 gat gaa caa gac cct cag gag gtg acg tac gca cag ttg gat cac tgc    1213
Asp Glu Gln Asp Pro Gln Glu Val Thr Tyr Ala Gln Leu Asp His Cys
    370             375             380 gtt ttc ata cag aga aaa atc agt cgc cct tct cag agg ccc aag aca    1261
Val Phe Ile Gln Arg Lys Ile Ser Arg Pro Ser Gln Arg Pro Lys Thr
385             390             395 ccc cta aca gat acc agc gtg tac acg gaa ctt cca aat gct gag ccc    1309
Pro Leu Thr Asp Thr Ser Val Tyr Thr Glu Leu Pro Asn Ala Glu Pro
400             405             410             415
```

```
aga tcc aaa gtt gtc tcc tgc cca cga gca cca cag tca ggt ctt gag    1357
Arg Ser Lys Val Val Ser Cys Pro Arg Ala Pro Gln Ser Gly Leu Glu
                420                 425                 430 ggg gtt ttc tag ggagacaaca gccctgtctc aaaacc                       1395
Gly Val Phe  *

<210> SEQ ID NO 4
<211> LENGTH: 434
<212> TYPE: PRT
<213> ORGANISM: Homo sapiens

<400> SEQUENCE: 4

Leu Met Gly Gly Gln Asp Lys Pro Phe Leu Ser Ala Arg Pro Ser Thr
 1               5                  10                  15

Val Val Pro Arg Gly Gly His Val Ala Leu Gln Cys His Tyr Arg Arg
             20                  25                  30

Gly Phe Asn Asn Phe Met Leu Tyr Lys Glu Asp Arg Ser His Val Pro
         35                  40                  45

Ile Phe His Gly Arg Ile Phe Gln Glu Ser Phe Ile Met Gly Pro Val
     50                  55                  60

Thr Pro Ala His Ala Gly Thr Tyr Arg Cys Arg Gly Ser Arg Pro His
 65                  70                  75                  80

Ser Leu Thr Gly Trp Ser Ala Pro Ser Asn Pro Val Val Ile Met Val
                 85                  90                  95

Thr Gly Asn His Arg Lys Pro Ser Leu Leu Ala His Pro Gly Pro Leu
            100                 105                 110

Leu Lys Ser Gly Glu Thr Val Ile Leu Gln Cys Trp Ser Asp Val Met
        115                 120                 125

Phe Glu His Phe Phe Leu His Arg Glu Gly Ile Ser Glu Asp Pro Ser
    130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
            180                 185                 190

Asp Ile Val Ile Thr Gly Leu Tyr Glu Lys Pro Ser Leu Ser Ala Gln
        195                 200                 205

Pro Gly Pro Thr Val Gln Ala Gly Glu Asn Val Thr Leu Ser Cys Ser
    210                 215                 220

Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg Ala Leu Pro Cys Val Trp Ser Asn Ser Ser Asp
        275                 280                 285

Pro Leu Leu Val Ser Val Thr Gly Asn Pro Ser Ser Ser Trp Pro Ser
    290                 295                 300

Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
                325                 330                 335

Phe Leu Leu Tyr Arg Trp Cys Ser Asn Lys Lys Asn Ala Ala Val Met
            340                 345                 350
```

-continued

```
Asp Gln Glu Pro Ala Gly Asp Arg Thr Val Asn Arg Gln Asp Ser Asp
            355                 360                 365

Glu Gln Asp Pro Gln Glu Val Thr Tyr Ala Gln Leu Asp His Cys Val
            370                 375                 380

Phe Ile Gln Arg Lys Ile Ser Arg Pro Ser Gln Arg Pro Lys Thr Pro
385                 390                 395                 400

Leu Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
                420                 425                 430

Val Phe

<210> SEQ ID NO 5
<211> LENGTH: 21
<212> TYPE: DNA
<213> ORGANISM: Artificial Sequence
<220> FEATURE:
<223> OTHER INFORMATION: up SC5 primer

<400> SEQUENCE: 5
catgtctgct cactggtcgt c                                              21

<210> SEQ ID NO 6
<211> LENGTH: 18
<212> TYPE: DNA
<213> ORGANISM: Artificial Sequence
<220> FEATURE:
<223> OTHER INFORMATION: down SC5 primer

<400> SEQUENCE: 6
ggttttgaga cagggctg                                                  18
```